US012350184B2

(12) United States Patent
Gefen

(10) Patent No.: US 12,350,184 B2
(45) Date of Patent: Jul. 8, 2025

(54) PRESSURE ABSORBING SKIN PATCH AND METHOD OF MANUFACTURING SAME

(71) Applicant: RAMOT AT TEL-AVIV UNIVERSITY LTD., Tel Aviv (IL)

(72) Inventor: Amit Gefen, Ganei Tikva (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 911 days.

(21) Appl. No.: 17/310,713

(22) PCT Filed: Feb. 18, 2020

(86) PCT No.: PCT/IL2020/050183
§ 371 (c)(1),
(2) Date: Aug. 19, 2021

(87) PCT Pub. No.: WO2020/170247
PCT Pub. Date: Aug. 27, 2020

(65) Prior Publication Data
US 2022/0183872 A1 Jun. 16, 2022

(30) Foreign Application Priority Data
Feb. 19, 2019 (IL) .......................................... 264911

(51) Int. Cl.
*A61F 5/32* (2006.01)
*A61F 5/34* (2006.01)
(Continued)

(52) U.S. Cl.
CPC .................. *A61F 5/32* (2013.01); *A61F 5/34* (2013.01); *A61F 7/02* (2013.01); *A61M 35/00* (2013.01);
(Continued)

(58) Field of Classification Search
CPC ...... A61F 5/32; A61F 5/34; A61F 7/02; A61F 13/069; A61M 35/00; A41D 31/00;
(Continued)

(56) References Cited

U.S. PATENT DOCUMENTS 5,066,494 A 11/1991 Becher
5,356,372 A 10/1994 Donovan et al.
(Continued)

FOREIGN PATENT DOCUMENTS

WO 2017/120682 A1 7/2017

OTHER PUBLICATIONS

Acorda, "Nursing and Respiratory Collaboration Prevents BiPAP-Related Pressure Ulcers", J Pediatr Nurs., 2015, vol. 30, No. 4, pp. 620-623.
(Continued)

*Primary Examiner* — Alireza Nia
*Assistant Examiner* — Daniel A Miller
(74) *Attorney, Agent, or Firm* — Vorys, Sater, Seymour and Pease LLP; Anthony P. Venturino; Maryellen Feehery Hank

(57) ABSTRACT

Provided is a patch including at least one pressure-absorbing member, the pressure absorbing member formed of a resilient material and having at least a first surface, the at least first surface is configured with a plurality of projections extending therefrom and a plurality of channels crossing one another at a plurality of intersections, an outermost surface of said plurality of projections lies along a projections plane of the pressure-absorbing member, the projections being deformable when subjected to pressure applied to the patch, so as to absorb at least some of the applied pressure.

18 Claims, 18 Drawing Sheets

(51) Int. Cl.
| | |
|---|---|
| A61F 7/02 | (2006.01) |
| A61F 13/06 | (2006.01) |
| A61M 35/00 | (2006.01) |
| B29C 39/12 | (2006.01) |
| B29L 31/00 | (2006.01) |

(52) U.S. Cl.
CPC .......... B29C 39/123 (2013.01); *A61F 13/069* (2013.01); *B29L 2031/753* (2013.01)

(58) Field of Classification Search
CPC .......... A41D 31/005; B23B 3/12; B23B 3/30; B32B 5/02; B32B 5/06; A61L 15/42; A61L 15/24; A61L 15/60; A61L 15/26; A61L 15/58; A61L 15/425
USPC ........................................................ 128/889
See application file for complete search history.

(56) References Cited

U.S. PATENT DOCUMENTS

| | | | |
|---|---|---|---|
| 7,745,682 B2 | 6/2010 | Sigurjonsson et al. | |
| 9,060,842 B2 | 6/2015 | Karp et al. | |
| 9,107,989 B2 | 8/2015 | Olson et al. | |
| 2016/0166422 A1* | 6/2016 | Karim .................. | A61F 5/34 128/889 |
| 2016/0250373 A1* | 9/2016 | Munro ................ | A61F 13/0206 602/48 |
| 2018/0184732 A1* | 7/2018 | Plant ........................ | B32B 3/26 |
| 2018/0333288 A1 | 11/2018 | Squires et al. | |

OTHER PUBLICATIONS

Baharestani et al., " Pressure Ulcers in Neonates and Children: An NPUAP White Paper", Advances in Skin & Wound Care, vol. 20, No. 4, pp. 208-220.
Barakat-Johnson et al., "Medical device-related pressure injuries: An exploratory descriptive study in an acute tertiary hospital in Australia", J Tissue Viability, 2017, vol. 26, No. 4, pp. 246-253.
Black et al., "Medical device related pressure ulcers in hospitalized patients", Int Wound J., 2010, vol. 7, No. 5, pp. 358-365.
Boesch et al., "Prevention of Tracheostomy-related Pressure Ulcers in Children", Pediatrics, 2012, vol. 129, No. 3, pp. e792-e797.
Clay et al., "Device Related Pressure Ulcers Pre and Post Identification and Intervention", J Pediatr Nurs., 2018, vol. 41, pp. 77-79.
Coyer et al., "A prospective window into medical device-related pressure ulcers in intensive care", Int Wound J., 2014, vol. 11, No. 6, pp. 656-664.
Gefen, "The future of pressure ulcer prevention is here: Detecting and targeting inflammation early", EWMA Journal, 2018, vol. 19, No. 2, pp. 7-13.
Ham et al., "Pressure ulcers in trauma patients with suspected spine injury: a prospective cohort study with emphasis on device-related pressure ulcers", Int Wound J., 2017, vol. 14, No. 1, pp. 104-111.
Kayser et al., "Prevalence and Analysis of Medical Device-Related Pressure Injuries: Results from the International Pressure Ulcer Prevalence Survey", Adv Skin Wound Care, 2018, vol. 31, No. 6, pp. 276-285.
Levy et al., "Adjustability and Adaptability Are Critical Characteristics of Pediatric Support Surfaces", Adv Wound Care, 2015, vol. 4, No. 10, pp. 615-622.
Levy et al., "Device-related pressure ulcers from a biomechanical perspective", J Tissue Viability, 2017, vol. 26, No. 1, pp. 57-68.
Levy et al., "Penile compression clamps: A model of the internal mechanical state of penile soft tissues", Neurourol Urodyn., 2017, vol. 36, No. 6, pp. 1645-1650.
Lustig et al., "Beware of the toilet: The risk for a deep tissue injury during toilet sitting", J Tissue Viability, 2018, vol. 27, No. 1, pp. 23-31.
Murray et al., "Medical Device-Related Hospital-Acquired Pressure Ulcers in Children: An Integrative Review", J Pediatr Nurs., 2013, vol. 28, No. 6, pp. 585-595.
Domens et al., "A numerical study to analyse the risk for pressure ulcer development on a spine board", Clin Biomech, vol. 28, No. 7, pp. 736-742.
O'toole et al., "Prevention of Tracheostomy-Related Hospital-Acquired Pressure Ulcers", Otolaryngol Head Neck Surg., vol. 156, No. 4, pp. 642-651.
Worsley et al., "Investigating the effects of cervical collar design and fit on the biomechanical and biomarker reaction at the skin", Med Devices, 2018, vol. 11, pp. 87-94.
Yamaguti et al., "Treatment-Related Risk Factors for Development of Skin Breakdown in Patients With Acute Respiratory Failure Undergoing Noninvasive Ventilation or CPAP", Respir Care, 2014, vol. 59, No. 10, pp. 1530-1536.

* cited by examiner

PRESSURE ABSORBING SKIN PATCH AND METHOD OF MANUFACTURING SAME

TECHNOLOGICAL FIELD

The invention relates to skin patches for use on the skin of patients, for preventing and treating pressure-related skin conditions. Another aspect of the disclosure is directed to skin-protecting pads configured to bear and disperse loads.

BACKGROUND ART

References considered to be relevant as background to the presently disclosed subject matter are listed below:
Baharestani M M, Ratliff C R. Pressure ulcers in neonates and children: An NPUAP white paper. ADVANCES IN SKIN & WOUND CARE & VOL. 20 NO. 4, 208-220.
Black J M, Cuddigan J E, Walko M A, Didier L A, Lander M J, Kelpe M R. Medical device related pressure ulcers in hospitalized patients. Int Wound J. 2010 October; 7(5):358-65.
Clay P, Cruz C, Ayotte K, Jones J, Fowler S B. Device related pressure ulcers pre and post identification and intervention. J Pediatr Nurs. 2018 Jan. 31. pii: S0882-5963(17)30546-8.
Coyer F M, Stotts N A, Blackman V S. A prospective window into medical device-related pressure ulcers in intensive care. Int Wound J. 2014 December; 11(6):656-64.
Gefen, A., The future of pressure ulcer prevention is here: Detecting and targeting inflammation early. EWMA Journal, 2018 19(2): p. 7-13.
Ham W H, Schoonhoven L, Schuurmans M J, Leenen L P. Pressure ulcers in trauma patients with suspected spine injury: a prospective cohort study with emphasis on device-related pressure ulcers. Int Wound J. 2017 February; 14(1):104-111.
Kayser S A, VanGilder C A, Ayello E A, Lachenbruch C. Prevalence and analysis of medical device-related pressure injuries: Results from the International Pressure Ulcer Prevalence Survey. Adv Skin Wound Care. 2018 June; 31(6):276-285.
Levy A, Kopplin K, Gefen A. Device-related pressure ulcers from a biomechanical perspective. J Tissue Viability. 2017 February; 26(1):57-68.
O'Toole T R, Jacobs N, Hondorp B, Crawford L, Boudreau L R, Jeffe J, Stein B, LoSavio P. Prevention of tracheostomy-related hospital-acquired pressure ulcers. Otolaryngol Head Neck Surg. 2017 April; 156(4):642-651.
Worsley P R, Stanger N D, Horrell A K, Bader D L. Investigating the effects of cervical collar design and fit on the biomechanical and biomarker reaction at the skin. Med Devices (Auckl). 2018 Mar. 15; 11:87-94.

Acknowledgement of the above references herein is not to be inferred as meaning that these are in any way relevant to the patentability of the presently disclosed subject matter.

BACKGROUND

Pressure ulcers, also termed pressure injuries, are a known and common problem in the care of medical patients of all ages, and in a variety of care facilities, particularly when patients are in one or more of the following situations, for example: confined to bed or a wheelchair, connected to medical devices, connected by tubing to medical equipment, having limited or no mobility e.g. due to a neuromuscular disease, muscle atrophy, spinal cord or brain injury, stroke, systemic or regional anesthesia, loss of consciousness, impaired with respect to sensory abilities such as the ability to detect discomfort or perceive pain, and incapable of communication with caregivers.

One type of pressure ulcer (PU) or pressure injury (PI), also known in the literature, or known in the past, as a pressure sore, bedsore or decubitus ulcer, occurs in patients who have temporary or permanent sensory and/or mobility impairments. Individuals who are insensate or immobile are typically confined to bed, are chair-bound or wheelchair users (e.g. due to a neuromuscular disease, central nervous system trauma or damage, or stroke) or are under anesthesia (e.g. while undergoing a surgery or medical examinations requiring general or partial anesthesia or analgesia), or are in an unconscious or partially-conscious state or under medications or drugs that compromise neuromuscular function (sensation and/or movement) e.g., as occurs further to use of epidural anesthesia. In such individuals, bodyweight forces cause sustained, large soft tissue deformations that gradually compromise cell and tissue viability via mechanisms of direct deformation-inflicted cell damage, secondary inflammatory damage (e.g. due to edema), potential ischemic damage due to reduced blood perfusion, damage due to impaired lymphatic function and waste clearance away from the affected tissues, and ischemia-reperfusion injuries. All these cell and tissue damage pathways originate from and/or relate to the exposure of cells and tissues to the sustained mechanical deformations as bodyweight forces are not relieved due to the impaired sensory and/or mobility condition. Under such conditions, cell death and tissue damage typically develop at regions of transfer of high bodyweight forces to the supporting surface/s, for example at the sacrum, heel and elbow regions.

Another type of PU or PI, known by the term medical device-related pressure ulcer (MDRPU) or medical device-related pressure injury (MDRPI) can be caused by devices designed and applied mostly for diagnostic or therapeutic purposes. In MDRPIs, the forces are applied externally by a medical or other device that contacts the skin of a patient and potentially applies pressure and shear on the skin at the contact surfaces. While the cell death and tissue damage pathways in MDRPIs are similar to those in general PIs (caused by sustained bodyweight forces), MDRPIs are typically caused by mechanical forces applied by the device or that are associated with use of the device. Oxygen masks, endotracheal tubes (ETTs), nasogastric tubes (NGTs), oxygen tubing, pulse oximeters, cervical collars, external fixators such as bone fixators, stoma equipment and tubing, electrocardiogram and encephalogram electrodes and wires, wireless devices, wearable devices, spine boards and urinary catheters, are a few examples of medical devices which can cause MDRPIs through application of mechanical forces via contact with the skin (including the lips, mucosal tissues of the nose etc.) or when placed between the body and a support surface (e.g. objects located between the body and mattress or cushion or spine board) which causes tissue distortion at and around the site of contact with the device or object.

PIs including MDRPIs can be serious injuries which can further be complicated by soft tissue infections, bone infections (osteomyelitis) and sepsis as well as by renal (kidney) failure (as the kidneys are not able to manage the degradation, and proteolysis in necrotic tissues), leading to multiple organ dysfunction—all are serious and life-threatening conditions. In addition to the above life-endangering states, scarring and hair loss resulting from PIs or MDRPIs which healed can have lifelong psychological effects.

It is often advantageous to introduce pads so as to absorb pressure applied to body parts by external objects, such as the shoulder straps or hip belts of a backpack, footwear, etc. Cushioning pads are generally known in the art.

Hereinafter in the specification and the claims, the terms pads and patches are used interchangeably.

GENERAL DESCRIPTION

The presently disclosed subject matter is concerned with a protective patch for the skin of a patient, which can be used to halt or reduce damage to the skin, subdermal and deep soft tissues exposed to the risk of pressure ulcer or pressure injury by absorbance of mechanical and thermal energy.

For the sake of clarity, the terms below shall have the meanings provided throughout the present description and claims: The term skin will be used to denote skin, subdermal and deeper soft tissues of a body, such as the body of a patient. It is noted that the body could be the body of a human or of an animal upon which pressure from an external source can be applied. The term PI will be used to denote any type of pressure related ulcer or injury, including medical device-related pressure ulcer (MDRPU) and medical device-related pressure injury (MDRPI). The term pressure will be used to denote any kind of pressure, including focal pressure, shear stress, and pressure caused by any directly or indirectly exerted forces, e.g., normal forces, shear forces, frictional forces, etc. The term medicament will be used to denote any kind of skin-protectant or therapeutic material used on the skin to provide protection to and/or healing of skin exposed to the risk of pressure-related injury.

A first aspect of the presently disclosed subject matter is directed to a patch comprising at least one pressure-absorbing member formed of a resilient material and having at least a first surface. The first surface of the pressure-absorbing member can be configured with a plurality of projections extending therefrom and a plurality of channels crossing one another at a plurality of intersections. An outermost surface of the plurality of projections can lie along a projections plane of the pressure-absorbing member. The projections can be deformable when subjected to pressure applied to the patch, so as to absorb at least some of the applied pressure. The patch can be configured such that the first surface or the projections plane of the pressure absorbing member can be a skin-engaging surface of the patch, which can engage, directly or indirectly, the skin of a patient. The patch can further be configured to have a pressure-engaging surface which can receive an external pressure applied to the patch.

In an alternative embodiment, the patch can be configured such that the first surface or the projections plane of one of the pressure-absorbing members of the patch, is the pressure-engaging surface of the patch.

In some embodiments of the patch according to the presently disclosed subject matter, the skin-engaging surface of the patch and the pressure-engaging surface of the patch can be opposite surfaces of the patch.

The pressure-engaging surface of the patch can be configured to receive a pressure exerted upon it by an external pressure-producing source. Such an external pressure-producing source can be, for example, an element of a medical device, equipment, or consumable which can be in contact with the body of a patient, e.g. oxygen masks, any ventilation, feeding or urinary equipment and tubing, electrodes of any type and their wiring, stoma care devices, orthotics and prosthetics, bone fixators, orthopedic equipment, sensors and monitoring equipment, e.g., pulse oximeters or glucose monitors, wireless devices and wearable devices, etc. Wireless devices and wearable devices can be, for example, such as those used for monitoring patient movements in bed, repositioning, or events of patients leaving the bed or returning to bed in hospitals or long-term care.

In some embodiments of the patch according to the presently disclosed subject matter, particularly those in which at least a portion of the external pressure on the skin results from a support surface exerting a reactive support force opposite a weight force of a body part of a patient, the skin-engaging surface of the patch and the pressure-engaging surface of the patch can be the same surface of the patch, which can be opposite from a support-engaging surface of the patch. The support-engaging surface of the patch can bear against an element which provides support to a patient, e.g., a mattress of a bed, or a seat, such as that of a wheelchair, car, bedside chair, shower stool or toilet, or a head support or arm support of a wheelchair.

It will be appreciated that the skin-engaging surface can be applied directly over the skin of an individual, or over a layer of clothing. For example, the skin-engaging surface can be applied to a heel of an individual wearing a sock, over the sock. Another example could be applying a pad under a shoulder strap of a backpack wherein the skin-engaging surface would bear over a garment (e.g., a shirt).

The patch can thus protect the skin of a body from an external pressure applied thereto, since the external pressure can be converted into another mechanical form, i.e., elastic or viscoelastic deformations of the projections of the patch.

The resilient material can be any suitable resilient material, e.g., soft polymer, elastomer, silicone, silicone rubber (e.g., transparent room temperature vulcanizing silicone rubber, polydimethylsiloxane, vinyl methyl), silicone sponge, rubber (e.g., neoprene, ethylene-vinyl acetate or poly-ethylene-vinyl acetate), gel (e.g., polymer gel, silicone gel or hydrogel), gel sponge, foam (e.g., silicone foam, gel foam, open-cell foam, closed-cell foam, etc.), fabric, polymer composite (i.e. multi-phase material in which one or more fillers are integrated with a polymer matrix), or any suitable combination thereof.

Selection of a resilient material for use in the patch can preferably take into account considerations pertaining to management of the microclimate at the contact area between the patch and the skin of a patient. That is, the resilient material for the patch can be selected so as to maximize heat loss from the skin, so as to maintain colder skin temperatures, thereby reducing the metabolic demands of the tissues. The resilient material can therefore be selected to have a specific heat capacity which is greater than that of skin of a patient.

The resilient material can further be selected to have thermal conductivity that is greater than that of skin of a patient. The resilient material can further be selected to have a high thermal conductance or low thermal resistance, so that when refrigerated prior to use, the patch can function as a coolant when applied to the body of a patient, conducting heat produced by the body tissues away from the body.

It is noted that the patient can be a human patient or an animal patient.

The projections plane of the patch can be disposed at a distance of a thickness of the pressure-absorbing member from the first surface of the pressure-absorbing member.

The plurality of channels in the patch can have uniform or varying lengths, and they can cross one another at a plurality of intersections.

A plane of the patch in which the plurality of channels is disposed can be parallel to the first surface of the pressure-absorbing member and disposed at a distance from it.

The projections can have any suitable shape, such as a cuboid or circular shape or a shape conforming to that of a specific object or device, or to body contours at a specific anatomical region.

The channels can have any suitable cross-sectional shape, such as circular, elliptical, rectangular, or any other polygonal shape. The channels can be the void spaces disposed in between the projections.

The pressure-absorbing member can be a two-faced pressure-absorbing member, wherein the first surface of the pressure-absorbing member and a second surface of the pressure-absorbing member are each configured with a plurality of projections extending therefrom and a plurality of channels crossing one another at a plurality of intersections. Furthermore, an outermost surface of a plurality of first projections extending from the first surface can lie along a first projections plane of the two-faced pressure-absorbing member, and an outermost surface of a plurality of second projections extending from the second surface can lie along a second projections plane of the two-faced pressure-absorbing member.

The patch can further comprise a sealing layer formed of the resilient material, wherein the sealing layer is disposed along the projections plane and connected to the plurality of projections so as to enclose the channels and form enclosed channels therebetween.

The sealing layer can be an additional pressure-absorbing member.

The patch can comprise a first pressure-absorbing member and a sealing layer which is an additional pressure-absorbing member, wherein the two pressure-absorbing members are oriented with respect to one another in a face-to-face manner, such that the projections plane of the first pressure absorbing member faces the projections plane of the additional pressure-absorbing member.

The patch can comprise a first pressure-absorbing member and a sealing layer which is an additional pressure-absorbing member, wherein the two pressure-absorbing members are oriented with respect to one another in a face-to-back manner, such that the projections plane of the first pressure absorbing member and the projections plane of the additional pressure-absorbing member face in the same direction.

The patch can comprise a first pressure-absorbing member and an additional pressure-absorbing member, wherein the two pressure-absorbing members are oriented with respect to one another in a back-to-back manner, such that the projections plane of the first pressure absorbing member faces in an opposite direction and away from the projections plane of the additional pressure-absorbing member.

The patch can further comprise one or more fluid reservoirs disposed along one or more of the channels of the plurality of channels.

The one or more fluid reservoirs can be disposed at one or more of the plurality of intersections at which the plurality of channels cross one another.

The reservoir or reservoirs disposed within the plurality of channels can contain a fluid, and the patch can be configured such that when the projections are deformed under an external pressure applied upon at least a portion of a surface of the patch, the fluid is propelled from at least one of the fluid reservoirs so as to flow at least into the channel adjacent to the fluid reservoir, wherein a frictional force between the fluid and the channel walls, absorbs at least a portion of the external pressure applied to the patch.

A fluid reservoir can be disposed at a portion of, or at all, of the intersections at which the plurality of channels cross one another.

The fluid in the reservoirs can be a viscous fluid.

As mentioned previously with respect to the selection of a resilient material for use in the patch, selection of the fluid for use in the reservoirs of the patch can also preferably take into account considerations pertaining to management of the microclimate at the contact area between the patch and the skin. That is, the fluid disposed in the fluid reservoirs of the patch can be selected so as to maximize heat loss from the skin, so as to maintain colder skin temperatures, thereby reducing the metabolic demands of the tissues.

The fluid disposed in the fluid reservoirs of the patch can therefore be selected to have a specific heat capacity which is greater than that of skin of a body, so that the fluid in the reservoirs can function as a medium for convective heat transfer, i.e., removal of skin-emitted thermal energy away from the site of application of the patch.

The fluid in the fluid reservoirs can be selected to have a high heat capacity so that when used subsequent to refrigeration, the fluid can function as a coolant, so as to remove heat away from the skin. As a non-limiting example, fluid in the reservoirs can contain the coolant betaine (trimethylglycine) which is produced from plants, is nontoxic and is easy to dispose of ecologically. In other possible embodiments, the fluid in the fluid reservoirs can contain oils such as mineral oils or silicone oils for the purpose of functioning as a coolant.

The fluid in the reservoirs can further contain one or more freezing point depressants such as alcohol (e.g., glycol) or salts, so that when the patch is refrigerated prior to use, the fluid in the patch can contribute to the maintenance of colder skin temperatures.

The flow of the fluid in a channel, or the plurality of channels of the patch, can further absorb external pressure applied to the patch, at least in part due to the friction between the fluid in the channel and the walls of the channel. The flow of fluids contained in the patch can dissipate energy at least in part by friction of the fluid against the walls of the channels.

Energy can also be dissipated by the viscous flow itself, thus allowing an additional portion of the external pressure applied to the patch to be absorbed.

The patch can comprise at least one resistance element disposed in at least one channel in the plurality of channels so as to increase the frictional force between the fluid and the channel walls, and/or the energy absorption of the viscous flow. The portion of the external pressure absorbed due to the frictional force between the fluid and the channel walls, and/or the additional portion of the external pressure absorbed due to the viscous flow, can thereby be increased.

A resistance element can be a blockage, obstruction, and/or valve disposed in a portion or all of the channels in order to increase the resistance imposed on the fluid flow and hence the resulting energy dissipation. For example, a portion or all of the channels can be filled to some extent with porous media so as to increase the resistance to the fluid flow and hence the resulting energy dissipation. Any restrictions or narrowing of the passages in the channels can similarly increase the resistance to the fluid flow and hence increase the resulting energy dissipation accordingly.

The patch can thus protect skin from external pressure applied thereto, by converting the external pressure into another mechanical form. Firstly, the patch can convert energy from the external pressure exerted upon it into deformation of the projections of the one or more pressure-absorbing members of the patch. Secondly, the patch can convert additional energy from the external pressure exerted upon it into compression of the fluid in the fluid reservoirs and propulsion of the fluid in the channels, optionally against additional resistance from porous media and/or other obstructions.

Either or both of a quantity of channels and a quantity of reservoirs, which together constitute a network of channels and reservoirs in a patch, can be varied, in combination with various combinations of restrictions, blockages and/or obstructions in some or all of the channels so as to allow the dissipation of mechanical energy in the patch to be adjusted, and thus the sensitivity and resolution of the patch can be adjustable to suit various applications.

The patch can have any shape, for example, a shape which can be described or roughly described by two dimensions, for example, a length and a width. The array of channels in the patch can comprise a first quantity of channels and a second quantity of channels. The first quantity of channels can be oriented in parallel with a first one of the dimensions, e.g., the length of the patch, and disposed at a distance from one another along the second one of the dimensions, e.g., the width of the patch. The second quantity of channels can be oriented in parallel with a second one of the dimensions, e.g., the width of the patch, and disposed at a distance from one another along the first one of the dimensions, e.g., the length of the patch. A plurality of reservoirs can be disposed at least at a portion of the intersections between the first quantity of channels and the second quantity of channels.

Another embodiment of the patch can have a shape which can be described or roughly described by a single dimension, for example, a diameter. The shape of the patch can have a central point and an outermost extent, and the array of channels in the patch can comprise a first quantity of channels and a second quantity of channels. The first quantity of channels can be a quantity of annular channels disposed at a distance from one another between an innermost annular channel disposed at a minimal distance from the central point of the patch, and an outermost annular channel disposed at a minimal distance from the outermost extent of the patch. The second quantity of channels can be a quantity of radiating channels extending in a radiating manner from the innermost annular channel to the outermost annular channel, and disposed at a distance from one another. A plurality of reservoirs can be disposed at least at a portion of the intersections between the annular channels and the radiating channels.

The annular channels can follow the shape of the patch, or they can have any other closed curved shape, such as circular, oval, any regular or non-regular polygonal shape, or any shape approximating or integrating one or a combination of the above shapes.

The patch can have a shape of a rectangle, a shape approximating a rectangle, non-regular or regular polygon, any curved shape or any combination thereof. The shape having an effective length in a vertical direction and an effective width in a horizontal direction, and the plurality of channels of the patch can comprise a first quantity of horizontal channels disposed at a distance from one another along the effective length of the shape, and a second quantity of vertical channels disposed at a distance from one another along the effective width of the shape, the horizontal channels and vertical channels intersecting one another at a plurality of intersections. One fluid reservoir or a plurality of fluid reservoirs can be disposed at least at a portion of the plurality of intersections.

In a patch having a shape of a rectangle, for example, the first quantity of horizontal channels can be disposed equidistantly or non-equidistantly from one another along the effective length of the shape, and the second quantity of vertical channels can be disposed equidistantly or non-equidistantly from one another along the effective width of the shape, the horizontal channels and the vertical channels thus forming a regular or non-regular grid, respectively.

A patch can have any number of channels, which can comprise any combination of straight channel segments and curved channel segments. A channel can have two ends. The two ends of a channel can face in opposite directions from one another, or alternatively, the two ends of a channel bending back along itself or toward itself, can face one another, or be oriented towards one another at any angle. A channel can form a closed circuit, or it can branch off into multiple channels.

The channels can be curved in a plane which is parallel to the plane of the first surface, second surface, or projections plane of the patch. Alternatively or additionally, the channels can be curved in a plane which is perpendicular to, or oriented at any angle to the plane of the first surface, second surface, or projections plane of the patch.

The channels can be curved in a plane which is parallel to the plane of the skin-engaging surface, pressure-engaging surface, or support-engaging surface of the patch. Alternatively or additionally, the channels can be curved in a plane which is perpendicular to, or oriented at any angle to the plane of the skin-engaging surface, pressure-engaging surface, or support-engaging surface of the patch.

The patch can be flexible and can be configured to be laid along, or secured to, a curved shape, for example, a concave shape or a convex shape, of a medical device or any other object that is in the patient's surroundings and with which the patient may come into contact. For example, a protective patch formed as a rectangular patch can be wrapped around a tube such as a nasogastric tube or endotracheal tube to form a patch in the shape of a tube. In another example, a protective patch can be shaped so as to fit along a portion of an oxygen mask which comes into contact with a patient's face, and it can be secured thereto, or alternatively formed as an integral part of the oxygen mask. In such an embodiment, the direction of the channels can follow the direction of the contours of the mask, or be oriented at an angle to the contours of the mask. In other embodiments, the patch can have the shape of segments of a cervical collar or a spine board, or be applied to cover the complete surfaces of these devices which may come into contact with a patient. For example, the channels can be tangent to the curves of the contours, perpendicular to the tangent lines of the curves, or oriented at any angle to the tangent lines of the curves, or any other reference line along the curves. Alternatively, the protective patch could have articulating means, so as to be articulated to the oxygen mask or other aforementioned devices or any other device or object.

The protective patch can be configured to have a stiffness which is matched to a stiffness of the skin at a location of its intended use, so as to reduce mechanical stress experienced by the skin.

The protective patch can be configured to have a stiffness that is a weighted average of the stiffness of the soft tissues at the location of intended use, e.g. thickness of the skin multiplied by stiffness of skin, plus thickness of subcutaneous fat multiplied by stiffness of subcutaneous fat, plus thickness of tendon multiplied by stiffness of tendon, and the sum of these terms being divided by the overall tissue thickness.

The protective patch can be configured to have thermal properties, including specific heat capacity of component materials and thermal conductive properties which are matched to the thermal properties of the skin at a location of its intended use, so as to reduce the trapping of heat at the patch-skin interface.

The patch can be configured to provide a visual indication regarding a measure of pressure applied to it. The fluid in the fluid reservoirs can be a colored fluid and the patch can be configured such that a measure of dispersion of the colored fluid in the channels can indicate a measure of the pressure applied to the patch. The fluid in the reservoirs (135) can be contained in capsules (136) that rupture, burst, or tear when the fluid reservoir sites are subjected to pressure.

The patch can thus be configured to provide an attention-grabbing visual indication, e.g. through the use of a brightly colored fluid (e.g. ink), that a medical device is exerting a dangerous pressure on the body of a patient. The patch can also be configured to provide the attention-grabbing visual indication by means of a color changing chemical reaction, for example when a fluid pushed from the fluid reservoirs crosses a reactive coating or meets a second fluid in one or more of the channels. The attention-grabbing visual indication can indicate to a caregiver that the medical device must be adjusted immediately in order to prevent harm from being caused to the patient. The attention-grabbing visual indication can indicate further that the patch which provided the attention-grabbing visual indication can no longer function so as to provide effective energy absorbance or pressure indication, and must therefore be discarded and replaced with a new patch.

The network of channels and reservoirs of the patch can be configured with additional customization so that the visual indication regarding a measure of pressure applied to the patch, can provide more detailed information about what measure of pressure is being exerted on the patch in particular areas of the patch, and whether a measure of pressure being exerted is below, above, or within a range of predetermined allowable limits for a safe measure of pressure.

For example, fluids disposed in particular reservoirs in particular locations of the patch can have different colors, so as to provide particularly colored visual indications in particular channels in particular areas of the patch when the differently colored fluids flow in the channels.

Non-colored fluids, or fluids of different colors disposed in reservoirs in particular locations of the patch can be fluids which change color when they come into contact with reactive coatings on the channel walls or with one another.

The fluids can be those which change color under a particular measure of pressure, or fluids which change color in accordance with a measure of pressure applied to them, e.g., piezochromic materials.

The channels can be graduated, i.e., marked with divisions or units of measurement, so that a dispersion of fluid in a channel can be measured, thereby giving an indication of the pressure exerted on the patch.

The channels can be configured to be transparent along particular segments of their lengths, and to be opaque along other particular segments of their lengths, so that a dispersion of fluid in a channel can be measured, thereby giving an indication of the pressure exerted on the patch and the time exposure to the pressure.

It is noted that throughout the present description and claims, the term transparent will be used to describe a material, which can be completely transparent, partially transparent, semitransparent, or translucent, such that changes of color, or the movement of colored fluid on an opposite side of the material can be observed.

A patch according to the presently disclosed subject matter can further be configured to release one or more medicaments onto the skin when subjected to a predetermined pressure. The patch can comprise medicament conduits for delivery of the medicament from the patch to the skin, each medicament conduit having an opening at each one of its two opposite ends, the first opening at a first end of the medicament conduit being disposed in a channel at a distance from at least one adjacent fluid reservoir, and a second opening at a second end of the medicament conduit being disposed at the skin-engaging surface of the patch.

The medicament can be disposed in a receptacle in the network of channels and reservoirs in the pressure-absorbing member.

In one embodiment, the medicament can be disposed in at least a portion of the channels at a distance from at least one adjacent fluid reservoir, and the patch can be configured such that when a pre-determined pressure is applied upon the pressure-engaging surface of the patch adjacent to the reservoir, the fluid released from the reservoir into the channels acts as a piston to push the medicament out of the medicament conduit onto the skin.

In another embodiment, the medicament can constitute the fluid in the fluid reservoir or reservoirs, and the patch can be configured such that when a pre-determined pressure is applied upon the pressure-engaging surface of the patch adjacent to a reservoir, the therapeutic material is released into at least one channel adjacent to the reservoir, and pushed out of a medicament conduit in the channel onto the skin.

In yet another embodiment, the medicament can be contained in capsules in the reservoirs, and the patch can be configured such that a pre-determined pressure applied upon the pressure-engaging surface of the patch adjacent to a fluid reservoir can cause the capsule to rupture, burst, or tear, thereby releasing the medicament into at least one channel adjacent to the fluid reservoir, and pushing it out of a medicament conduit in the channel onto the skin.

The medicament can be a substance which can be beneficial to the patient due to providing one or more of the following: tissue treatment, skin protection, barrier protection, pain reduction, lubrication, moisturization, nourishment.

The patch can be consumable and disposable.

The patch can comprise an exhaustion indication, configured so as to indicate when the patch needs to be replaced with a new patch.

Geometrical properties of the patch (e.g., shape and dimensions of the patch, quantities, shapes, dimensions, and positions of the channels, fluid reservoirs, and medicament conduits) can be varied to suit different applications associated with different parts of the body and/or different medical devices or other objects located in the vicinity of a patient, e.g. bed rails, board at the foot of the bed, transfer boards, bedside chairs, car and airplane seats.

The patch can be formed of two layers of material secured to one another. Each layer can be an identical pressure-absorbing member. The two pressure-absorbing members can be applied and secured to one another along their projections planes, such that the first plurality of channels and fluid reservoirs of the first pressure-absorbing member are aligned with the second plurality of channels and fluid reservoirs of the second pressure-absorbing member, so as to form enclosed channels and fluid reservoirs within the patch.

The material of the two-layer patch can be, for example, any polymer, elastomer or silicone such as transparent room temperature vulcanizing (RTV) silicone rubber or polydimethylsiloxane (PDMS) or vinyl methyl (VMQ) silicone rubber.

In other embodiments, the materials of a two-layer patch can be materials which are not identical to one another, for example, one layer can be made of gel, foam, or rubber, e.g., neoprene, ethylene-vinyl acetate (EVA) or poly-ethylene-vinyl acetate (PEVA), and the other layer can be made of silicone rubber. Such a combination can facilitate a graded-stiffness structure of the patch to enhance absorption of mechanical energy.

In yet other embodiments, the material of the patch can be made of recyclable materials such as soft cardboard or corrugated fiberboard materials.

It will be appreciated that the above list of materials is a list of exemplary materials and is not an inclusive list.

The patch can be formed of three layers of material secured together wherein the middle layer of the three layers is a pressure-absorbing member having a network of channels and reservoirs, and the medicament conduits are formed as holes between the channels and an opposite surface of the pressure-absorbing member. The holes can be oriented perpendicular to the plane of the skin-engaging surface of the patch. An outer layer can be secured to the pressure-absorbing member middle layer on each one of its two surfaces.

The two outer layers can provide mechanical load alleviation through cushioning. The pressure-absorbing member middle layer can have a different stiffness than the two outer layers, such that the multi-layered patch has a graded-stiffness through its layers.

The patch can be configured to have a plurality of layers, wherein a skin-engaging first layer of the patch has a stiffness matching that of the skin or a weighted stiffness of skin at an intended location of application of the patch on a body, and each upper layer of the patch has a decreasing measure of stiffness directly related to its increasing distance from the skin. This arrangement of a graded-stiffness can improve the energy absorption properties in the less stiff layers located further away from the skin, and can provide optimal stress-reduction at the level of the skin where the stiffness of the layer of the patch in closest proximity with the skin is matched to the stiffness of the skin at a location of intended use of the patch.

The patch can be configured to have a stiffness in its skin-engaging first layer which matches a characteristic skin stiffness or weighted average of tissue stiffness of a particular group of patch users, for example, diabetics, the elderly, overweight/obese patients, malnourished patients, pediatric patients, term or pre-term newborns.

The patch can furthermore have at least one layer having a varying stiffness along a plane parallel to the skin-engaging surface of the patch. Different areas of the patch in the same plane of the patch can thus have different stiffness values, so as to, for example, provide an area of the patch having increased protection from pressure and shear stress suitable for an especially sensitive location, e.g. the site of an incision, stitches, a surgical wound, or an existing traumatic or chronic wound.

The patch can be configured to have a plurality of layers, wherein at least one of the layers is a pressure-absorbing member such as described above.

In one example, a patch can comprise two layers, each layer being a pressure-absorbing member comprising a network of channels and fluid reservoirs, in which the channels have been enclosed so as to be enclosed channels. In such a patch, each of the pressure-absorbing member layers can operate separately. One or both of the pressure-absorbing member layer or layers, and any additional sealing, or other layers of the patch can be transparent, so that a visual indication of the pressure activity experienced by the patch can represent the fluid flow in the channels in both layers, one being superimposed upon the other and visible through the transparent layers.

In another example, the patch can be configured such that at least two of its layers which are pressure-absorbing members, each comprising a network of channels and reservoirs, can be interconnected by at least one interconnecting conduit running between them, perpendicularly or oriented at an angle to the skin-engaging surface, pressure-engaging surface, or support-engaging surface of the patch, such that a pressure activity causing a particular fluid flow in a first one of the layers can have a particular effect on a fluid flow in the second one of the layers. The patch can furthermore have an uppermost and/or an outermost transparent layer, such that a visual indication of the pressure activity experienced by the patch can include the fluid flow in the channels in both layers, one being superimposed upon the other and visible through the transparent layers.

The patch can be used for any situation of PI risk regardless of its nature. For example, the patch can be used on a portion of the body of an immobile and/or insensate patient, for example, a portion of the body having a bony prominence, such as the heels, elbows, shoulder blades, sacrum, occiput, ischial tuberosities or trochanters, which may be at risk for the development of a PI as a result of prolonged pressure imposed on that portion of the body by a supporting surface, due to a weight of at least a portion of the immobile and/or insensate body.

In the case of PI risk posed by weight of a body on a supporting surface, the patch could be placed between the at-risk body part and the supporting surface (e.g. as an overlay), and could be held in place by gravity, friction, hook-and-loop fasteners, hook-and-pile fasteners, or touch fasteners. As an alternative, the patch could be secured, for example by an adhesive material, to the skin of the patient in the region of the at-risk body part. Alternatively, the patch could be mounted on the support surface, for example, it could be attached to an aid device of the patient (e.g. mattress of a bed, or the seat of a wheelchair or to any part of a bed or chair which may be in contact with the body of a user such as the bedrails or armrests or back-rest or footrests).

In the case of a medical device-related pressure injury (MDRPI) risk, the patch can be used on a portion of the body at risk for the development of an MDRPI due to pressure exerted upon it by a medical device. Such medical devices can include, for example, oxygen masks, any ventilation, feeding or urinary equipment and/or tubing, e.g., endotracheal tubes (ETTs), nasogastric tubes (NGTs), oxygen tubing, urinary catheters, etc., electrodes of any type and their wiring, sensors and monitoring equipment, e.g., pulse oximeters, glucose monitors, etc., cervical collars, spine boards, bedpans, stoma devices and tubing, casts, orthotics, prosthetics, external fixators, e.g., bone fixators etc., orthopedic equipment, and wireless devices and wearable devices, such as those used for monitoring patient movements in bed, repositioning, or events of patients leaving the bed or returning to bed in hospitals or long-term care, etc. A positioner for a body part, for example, a head positioner on a wheelchair, could also be considered a medical device liable to present the risk of a PI to a body part which it is designed to hold in place.

In the case of MDRPIs, the patch or a plurality of identical or different patches could be placed between the at-risk body part and the medical device. Depending on the location and/or the orientation of the particular application, the patch or patches could be held in place by gravity, by friction, or by being wedged in between the medical device and the at-risk body part. That is, in some cases, the pressure applied by the medical device can hold the patch in place on the at-risk body part. As an alternative, the patch can be secured, for example, by an adhesive material to either the medical device, at least along the portion of the device which comes into contact with the skin of the patient, or to the skin of the patient in the region of the at-risk body part. In another alternative, the patch or patches can be formed as an integral part of the medical device or as a kit for use with the medical device.

The patch can include articulation arrangements for articulation to a medical device or aid device, such as a glucose pump, glucose meter, stoma, bedpan toilet seat, finger oximeter, arterial line and related securement device, central venous line and related securement device, drain devices, genital urinary devices, endotracheal or tracheostomy tubes, nasogastric tubes, ventilation masks and oxygen delivery devices, orthopedic devices, cervical collar, spine board, external fixators, e.g., bone fixators, other tubes and securement equipment, electrodes, e.g. electrocardiogram (ECG) or electromyogram (EMG) or electroencephalogram (EEG) electrodes, and other monitoring devices, such as wireless devices and wearable devices.

Articulation arrangements can include, for example, adhesives, hook-and-loop fasteners or hook-and-pile fasteners, touch fasteners, vacuum attachments, magnetic attachments, etc.

In an alternate embodiment, the articulation arrangement can be separate from the patch and can be articulatable to the patch and/or to the body.

The patch can be configured to have a particular size and shape, or it can be configured to be cut into a desired shape by a user of the patch or by a caregiver of a patch user.

The patch or multiple patches can be included in a kit comprising a medical device, wherein the patch in the kit is configured for use with the medical device in the kit.

Another aspect of the presently disclosed subject matter is directed to a method for producing a patch of the kind described above with respect to the previous aspects of the presently disclosed subject matter.

One exemplary method of producing a two-layer protective patch, each layer being formed of a pressure-absorbing member in accordance with the presently disclosed subject matter comprises:

Producing a negative mold of the network of reservoirs and channels designed for the patch, for example by three-dimensional (3D) printing;

preparing a mixture of a material out of which each of the two pressure-absorbing members of the protective patch can be formed;

pouring the mixture into the mold;

allowing the mixture to solidify so as to allow curing, for example, at room temperature;

separating the molded structure from the mold;

placing capsules of fluid or pipetting fluid at the locations of the fluid reservoirs; and applying and attaching, for example, by an adhesive, the two molded pressure-absorbing members produced by the above steps of pouring, allowing, and separating, at their projection planes, such that the arrangement of cavities of the network of reservoirs and channels of the pressure-absorbing members face one another.

The material out of which each of the two pressure-absorbing members of the protective patch can be formed can be any polymer, elastomer or silicone such as silicone rubber material, (e.g., transparent room temperature vulcanizing (RTV) silicone rubber, polydimethylsiloxane (PDMS), vinyl methyl (VMQ) silicone rubber, etc.), soft polymers, gels (e.g., polymer gel, silicone gel, hydrogel, etc.), foams (e.g., silicone foam, gel foam, open-cell foams, closed-cell foams, etc.), rubber (e.g., neoprene, ethylene-vinyl acetate (EVA), poly (ethylene-vinyl acetate) (PEVA), etc.), silicone sponge, gel sponge, or fabrics.

The step of allowing the mixture to solidify at room temperature to allow curing can be following by exposing the molded structure to heat, such as to a heat of 100° C., e.g. for approximately one hour, so as to enhance the curing process.

One exemplary method of producing a three-layer protective patch in accordance with this aspect of the presently disclosed subject matter comprises:

Producing a negative mold of the pressure-absorbing member forming the middle layer of the three-layer protective patch, for example, by 3D printing, of an arrangement of cavities for the network of channels and reservoirs of the pressure-absorbing member, and medicament conduit holes extending between the channels and a surface of the pressure-absorbing member, the holes being perpendicularly oriented with respect to the skin-engaging surface of the patch;

placing capsules of fluid at the locations of the reservoirs, or pipetting viscous fluid at the locations of the reservoirs;

placing one or more medicaments in one or more receptacles in the pressure-absorbing member;

preparing holes in a medicament delivery layer for release of a medicament through the medicament-delivery layer; and securing a sealing layer along the projections plane of the pressure-absorbing member, and the medicament-delivery layer along an opposite surface of the pressure-absorbing member so as to align the medicament conduit holes in the pressure-absorbing member with the perforations in the medicament delivery layer.

The middle layer comprising the pressure-absorbing member can be printed out of a variety of materials, such as soft polymers, silicone rubbers or other elastomers, silicones, rubbers, foams, or gels.

The outer layers can be transparent, semi-transparent, or opaque, e.g., by means of dense pigment in certain locations, and they can be transparent or semi-transparent in other locations, and can be formed of a variety of materials, such as any elastomer, silicone, soft polymers, silicone rubbers, foams or gels, etc.

In any of the above aspects, the patch can have features described above in any combination thereof.

It will be appreciated that the extent of energy absorbance of the patch is dependent upon the viscosity of the fluids contained in the patch, the permeability (e.g. existence of obstructions or blockage, porous media, valves or other means to obstruct the flow of the fluids in the channels of the patch, intended, by design, to provide resistance to the flow), the number of the channels connected to each fluid reservoir, the cross-sectional area of the channels, the lengths of individual channels and the cumulative length of channels.

Thus, the sensitivity of the patch can be pre-determined by the above-mentioned design parameters of the channels so that when the filling of the channels is visible in the patch, it can be concluded that a pre-determined exerted pressure and time exposure thresholds have been exceeded and thus, the patch has functioned to absorb a portion of the applied mechanical energy via the viscous flow of the fluid, and therefore has lost its full protective effect. The indicator mechanism of the patch can thus be customized for each particular application.

The arrangement of the disclosure suggests that an effective way to increase the absorbance of mechanical energy in the patch via flow of a viscous fluid is through increase in the cumulative length of channels. It is also the case that an increase in the number of channels, the viscosity of the viscous fluid or the cross-sectional area of the channels, or a decrease in the permeability of the channels are each also effective ways to increase the absorbance of the mechanical energy of the patch. Given the above-demonstrated theoretical efficiency of the network of channels in absorbing mechanical energy that can be applied by bodyweight forces and/or medical devices through viscous flow, it is noteworthy that the network of channels embedded in protective patches as described above facilitates mechanical energy absorbance via minimal thickness structures (i.e., mechanical energy transferred from external pressure is absorbed by flow in the channels in thin patches). In addition, the invention allows for immediate preventative interventions delivered where excess pressures have been applied.

Specifically, the absorbance of energy by means of viscous flow in channels may reduce the required volume and mass of mattresses, cushions, or positioners (e.g. for the head or heels) and other protective means used according to current art to prevent PIs in limited spaces (such as the ones listed above), by placing patches over thinner or firmer (stiffer) support surfaces. A patch or a plurality of patches may be used to cover an entire support surface or specific areas which are known to be associated with an increased risk for PIs, where the energy absorbance capacity of the patches substitutes, compensates for, or complements that of an existing, reduced-thickness or absence of a mattress, cushion, positioner, or other support surface.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
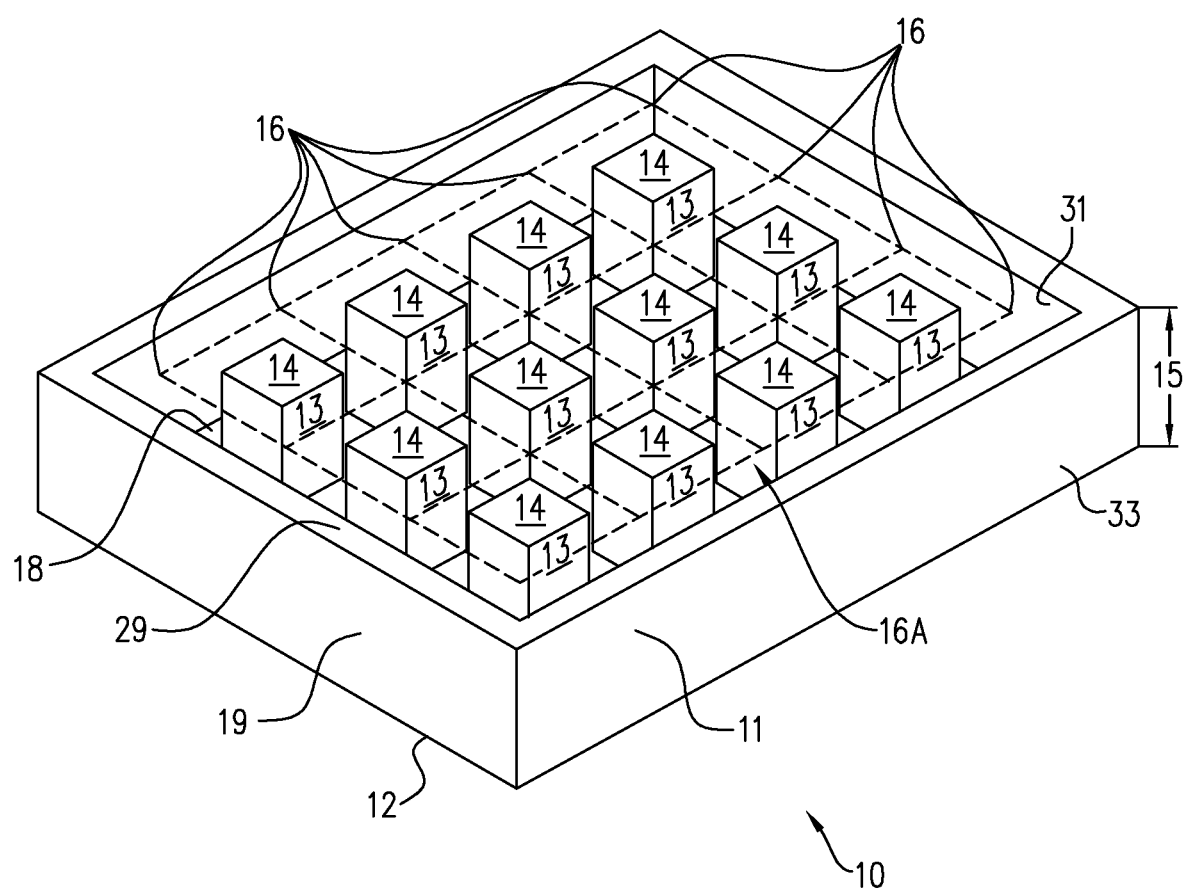
FIG. 1A is a top perspective view of a patch in accordance with an example of the presently disclosed subject matter.

FIG. 1A shows a patch 10, configured according to one embodiment of the presently disclosed subject matter, for placement on the skin of a patient in a location on the patient's body which is at-risk for the development of a pressure injury.

A patch in accordance with an embodiment of the presently disclosed subject matter, such as patch 10, can comprise at least one pressure absorbing member formed of a resilient material, having at least a first surface. The first surface can be configured with a plurality of projections extending therefrom, and a plurality of channels crossing one another at a plurality of intersections. An outermost surface of the plurality of projections can lie along a projections plane of the pressure-absorbing member, and the projections can be deformable when subjected to pressure applied to the patch, so as to absorb at least some of the applied pressure.

Figure 1B:
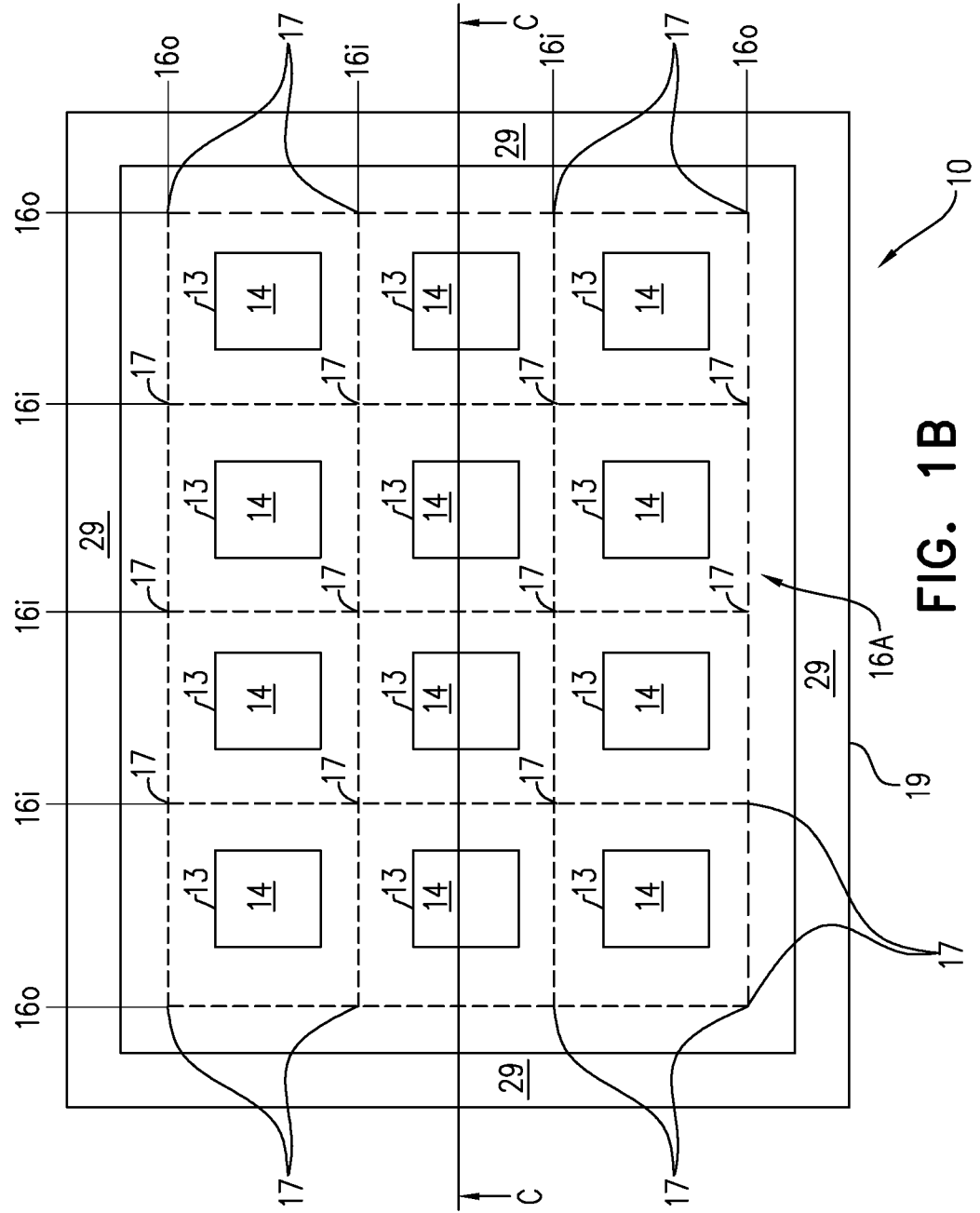
FIG. 1B is a top view of the patch of FIG. 1A.
Figure 1C:
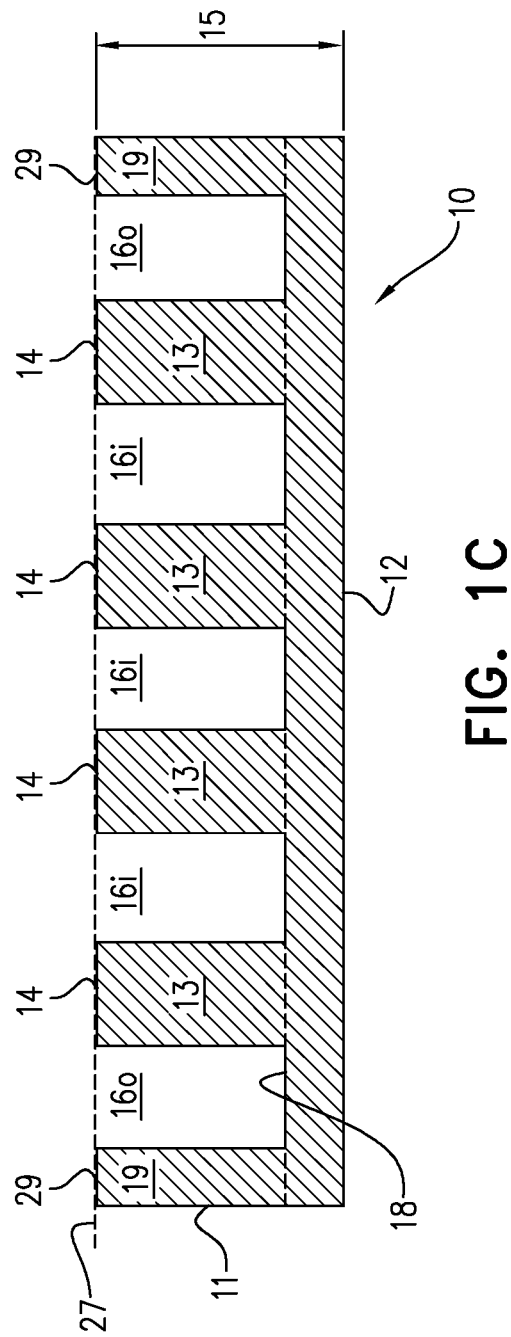
FIG. 1C is a cross-section of the patch of FIGS. 1A and 1B, taken along line C-C in FIG. 1B.

Accordingly, as shown in FIGS. 1A, 1B and 1C, the exemplary patch 10 comprises a pressure-absorbing member 11 formed of a resilient material, having a thickness 15, and having a first surface 12 and a second surface 18. In the exemplary patch 10, as can be seen in FIGS. 1A and 1C, it is the second surface 18 which is configured with a plurality of projections 13 extending therefrom, and a plurality of channels 16 crossing one another at a plurality of intersections 17, which can be seen in FIG. 1B. The plurality of channels 16 form an array of channels 16A. The projections 13 are deformable so as to absorb an external pressure applied to the patch.

As mentioned above, the term pressure will be used to denote any kind of pressure, including focal pressure, shear stress, and pressure caused by any directly or indirectly exerted forces, e.g., normal forces, shear forces and frictional forces.

The resilient material can be any suitable resilient material, e.g., elastomer, soft polymer, silicone, silicone rubber (e.g. transparent room temperature vulcanizing silicone rubber, polydimethylsiloxane, vinyl methyl), silicone sponge, rubber (e.g. neoprene, ethylene-vinyl acetate or poly-ethylene-vinyl acetate), soft polymer, gel (e.g., polymer gel, silicone gel or hydrogel), gel sponge, foam (e.g., silicone foam, gel foam, open-cell foam, closed-cell foam, etc.), fabric, polymer composite (i.e. multi-phase material in which one or more fillers are integrated with a polymer matrix), or any suitable combination thereof.

As further shown in FIG. 1A, the exemplary patch 10 is bounded by an outer bounding wall 19 which forms an outer perimeter of the patch 10. It will be appreciated that like the plurality of projections 13, the outer bounding wall 19 can be deformable so as to absorb an external pressure applied to the patch in a region of the outer bounding wall 19.

Each of the projections 13 can be seen to have an outermost surface 14 facing in an opposite direction from the first surface 12 and disposed at a distance therefrom. In the view of the patch 10 shown in FIG. 1A, the first surface 12 of the patch 10 is facing in a downward direction, while the outermost surfaces 14 of each of the projections 13 can be seen to be facing in an opposite, upward direction. The outermost surfaces 14 of each of the projections 13 can further be seen to be disposed at the distance of the thickness 15 of the pressure-absorbing member 11 from the first surface 12 of the patch 10. The outermost surfaces 14 of the projections 13 lie along a projections plane 27 of the pressure-absorbing member 11, indicated in FIG. 1C.

Like the plurality of projections 13, the outer bounding wall 19 of the exemplary patch 10 can be seen in FIG. 1A to have an outward-facing surface 29 facing upward, in an opposite direction from the first surface 12, and disposed at a distance of the thickness 15 of the pressure-absorbing member 11 from the first surface 12 of the patch 10.

It will be appreciated that the outer bounding wall 19 of the exemplary patch 10 further has an inner side surface 31 facing in an internal direction toward the projections 13, and an outer side surface 33 opposite the inner side surface facing in an external direction from the patch 10.

In FIG. 1B, the array of channels 16A of the patch 10 can be seen to be formed of the plurality of channels 16 crossing one another at a plurality of intersections 17.

It can furthermore be seen in FIGS. 1A, 1B and 1C that the void spaces disposed in between the projections 13 constitute a portion of the plurality of channels 16. In the exemplary patch 10, as can be seen in FIG. 1B, the void spaces disposed in between the projections 13 constitute five innermost channels 16i of the plurality of channels 16 in the array of channels 16A, while the void spaces disposed in between the projections 13 and the outer wall 19 constitute four outermost channels 16o of the plurality of channels 16 in the array of channels 16A.

In FIG. 1C, which shows a cross-section of the patch 10 of FIGS. 1A and 1B, taken where indicated by the letters C in FIG. 1B, three of the innermost channels 16i of the array of channels 16A can be seen in cross-section to be disposed in between the four projections 13 visible in cross-section in the figure, while two of the outermost channels 16o of the array of channels 16A can be seen in cross-section to be disposed in between the two outermost projections 13 and the outer wall 19 of the exemplary patch 10.

The patch can be configured such that either the first surface or the projections plane of one of the pressure-absorbing members of the patch, is a skin-engaging surface of the patch, and bears against, directly or indirectly, the skin of a patient, in an area of the patient's body which is prone to develop a PI. The surface of the patch which is opposite the skin-engaging surface, can be a pressure-engaging surface of the patch, configured to receive the application of an external pressure upon it.

In an alternative embodiment, the patch can be configured such that the first surface or the projections plane of one of the pressure-absorbing members of the patch, is the pressure-engaging surface of the patch, and the surface of the patch which is opposite the pressure-engaging surface, can be the skin-engaging surface of the patch.

In yet an alternative embodiment, particularly those in which at least a portion of the external pressure exerted on the skin results from a support surface exerting a reactive support force opposite a weight force of a body part of a patient, the skin-engaging surface of the patch and the pressure-engaging surface of the patch can be the same surface of the patch, which can be opposite from a support-engaging surface of the patch. The support-engaging surface of the patch can bear against an element which provides support to a patient, e.g., a mattress of a bed, or a seat, such as that of a wheelchair, car, bedside chair, shower stool or toilet, or a head support or arm support of a wheelchair.

Figure 8:
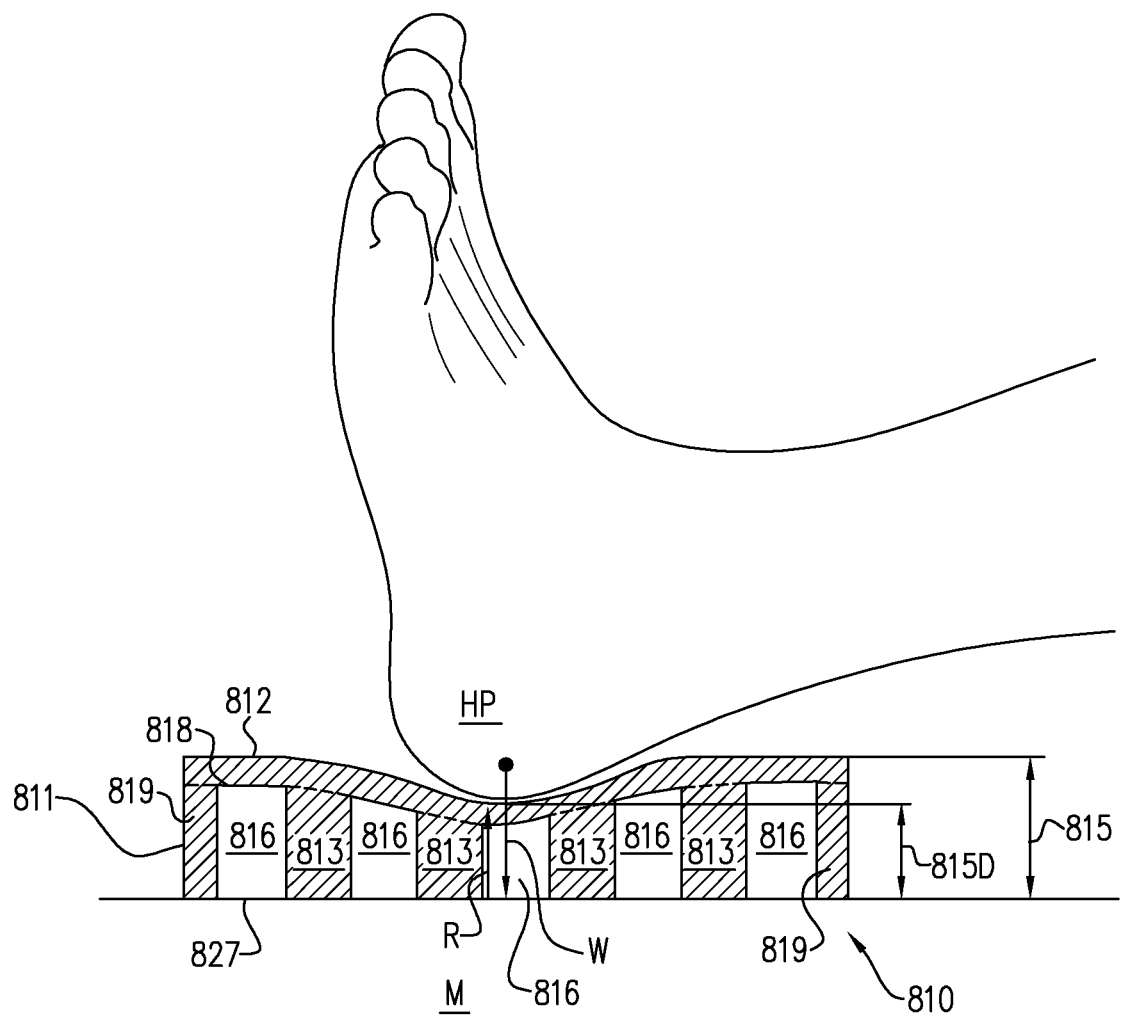
FIG. 8 is a cross-section of the patch of FIGS. 1A, 1B and 1C, shown in use.

For example, as shown in FIG. 8, an exemplary patch 810 can be seen to be positioned on a mattress M underneath a heel HP of a patient. The posterior aspect of the heel HP of the patient can be understood to be at-risk for the development of a PI due to its weight W exerted upon the mattress M, and the reaction force R consequentially exerted by the mattress M upon the heel HP of the patient. It is noteworthy that in addition to the vertical component of the reaction force R which occurs in reaction to the gravity force acting on the heel HP, and is shown in FIG. 8, the reaction force R can also typically have a horizontal component, which is not shown in FIG. 8, in reaction to a frictional force acting between the heel HP of the patient and the mattress M.

The patch 810 can be seen to be similar to the patch 10 shown in FIGS. 1A, 1B and 1C, having a single pressure-absorbing member 811 formed of a resilient material, the pressure-absorbing member 811 having a first surface 812 and a second surface 818. Like in the exemplary patch 10, shown in FIGS. 1A, 1B and 1C, it is the second surface 818 of the patch 810 which is configured with a plurality of projections 813 extending therefrom between a plurality of channels 816. It is noted that elements of the patch 810 which correspond to similar elements of the patch 10 in FIGS. 1A, 1B and 1C, have the same reference numerals as the corresponding elements of the patch 10, increased by 700.

It can further be seen in FIG. 8 that the exemplary patch 810 is configured and positioned such that the first surface 812 of the single pressure-absorbing member 811 of the patch 810 is the skin-engaging surface of the patch, bearing against the skin of the heel HP of the patient. As explained previously, since the external pressure exerted on the skin of the heel HP results from the support surface of the mattress M exerting the reactive support force R opposite the weight force W of the foot of the patient at the heel HP, the skin-engaging surface 812 of the patch 810 is also the pressure-engaging surface of the patch 810, while the surface of the patch 810 which is opposite the skin-engaging surface 812 is the support-engaging surface of the patch 810, which, as can be seen in FIG. 8, lies along the projections plane 827 of the pressure-absorbing member 811.

The patch 810 can be seen in FIG. 8 to be deformable so as to absorb an external pressure applied to the patch, as the patch 810 can be seen to have its undeformed thickness 815 at its outer bounding wall 819, while at a central area of the patch 810, the patch 810 can be seen to have been deformed by the weight W of the patient's heel HP, to a minimal deformed thickness of 815D. It will be appreciated that as a result of the above mentioned absorption of pressure by the patch 810, the patch 810 can provide protection to the patient's heel HP from a pressure injury.

It will be appreciated that the exemplary patch 810 could be held in place on the mattress M by a combination of gravity and friction, or alternatively, it could be connected, e.g., by adhesive, to the patient's heel HP. Yet alternatively, it could be mounted to the mattress M.

In another embodiment of a patch according to the presently disclosed subject matter, the pressure-absorbing member can be a two-faced pressure-absorbing member. The two-faced pressure-absorbing member can have a first surface and a second surface, each configured with a plurality of projections extending therefrom and a plurality of channels crossing one another at a plurality of intersections. An outermost surface of the plurality of first projections extending from the first surface can lie along a first projections plane of the two-faced pressure-absorbing member, and an outermost surface of the plurality of second projections extending from the second surface can lie along a second projections plane of the two-faced pressure-absorbing member.

Figure 14A:
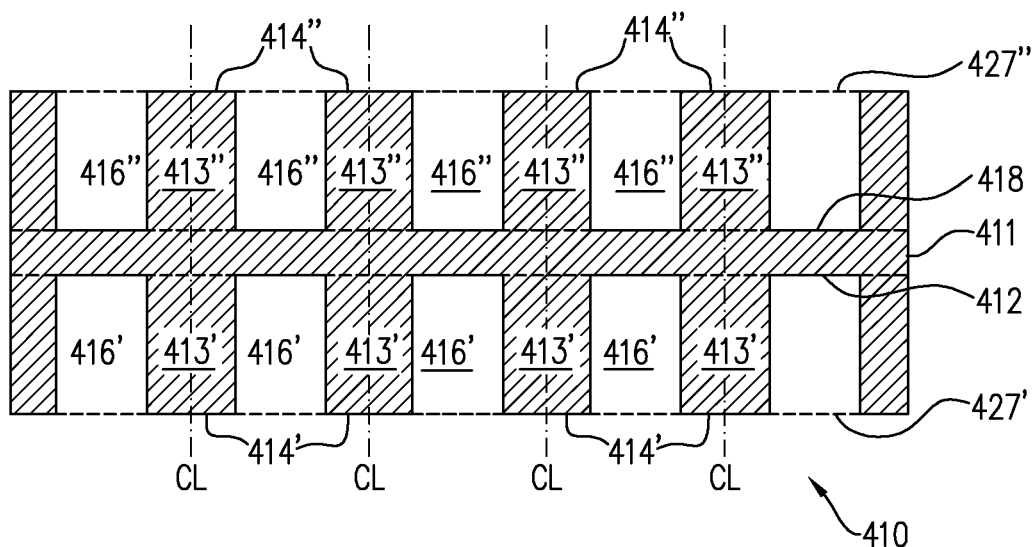
FIG. 14A is a cross-section of a patch in accordance with still another example of the presently disclosed subject matter.
Figure 14B:
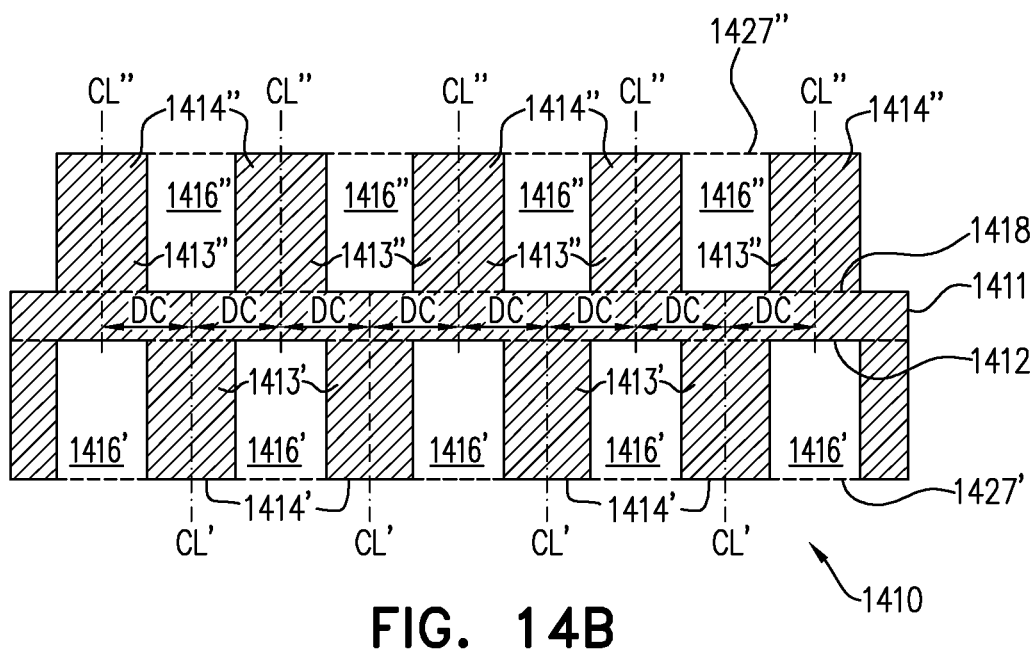
FIG. 14B is a cross-section of a patch in accordance with yet another example of the presently disclosed subject matter.

FIGS. 14A and 14B each show a cross-section of an exemplary patch 410 and 1410, respectively, comprising a two-faced pressure-absorbing member. It is noted that elements of the patches 410 and 1410 which correspond to elements of the patch 10 have the same reference numbers as those in the patch 10, increased by 400 and 1400 respectively.

As shown in FIG. 14A, the exemplary patch 410 has a first surface 412 and a second surface 418, each configured with a plurality of projections 413 extending therefrom and a plurality of channels 416, which, though it cannot be seen in the section view of FIG. 14A, can be understood to cross one another at a plurality of intersections, like the channels 16 of the patch 10 shown in FIGS. 1A, 1B and 1C.

In FIG. 14A, the plurality of first projections 413 extending from the first surface 412 and the plurality of channels 416 associated with the first surface 412 have the reference numbers 413' and 416', while the plurality of second projections 413 extending from the second surface 418 and the plurality of channels 416 associated with the second surface 418 have the reference numbers 413" and 416" respectively.

An outermost surface 414' of the plurality of first projections 413' extending from the first surface 412 lie along a first projections plane 427' of the two-faced pressure-absorbing member 411, and an outermost surface 414" of the plurality of second projections 413" extending from the second surface 418 lie along a second projections plane 427" of the two-faced pressure-absorbing member 411.

It will be appreciated that the exemplary patch 1410 shown in FIG. 14B is similar to the patch 410 shown in FIG. 14A, with corresponding elements of the patch 1410 having reference numbers corresponding to those of the patch 410. The patch 1410 is different from the patch 410 however, in that the projections 1413' and 1413" are not aligned with one another, as the projections 413' and 413" are aligned with one another as demonstrated by the centerlines CL passing through pairs of aligned projections 413' and 413". Rather, the projections 1413' and 1413" are staggered with respect to one another as the distances DC between the center lines CL' and CL" of the projections 1413' and 1413" indicate.

The patch according to the presently disclosed subject matter can further comprise a sealing layer formed of a resilient material. The sealing layer can be disposed along a projections plane of a pressure-absorbing member of the patch, and it can be connected to the plurality of projections of the pressure-absorbing member so as to enclose the channels and form enclosed channels between the projections.

Figure 2A:
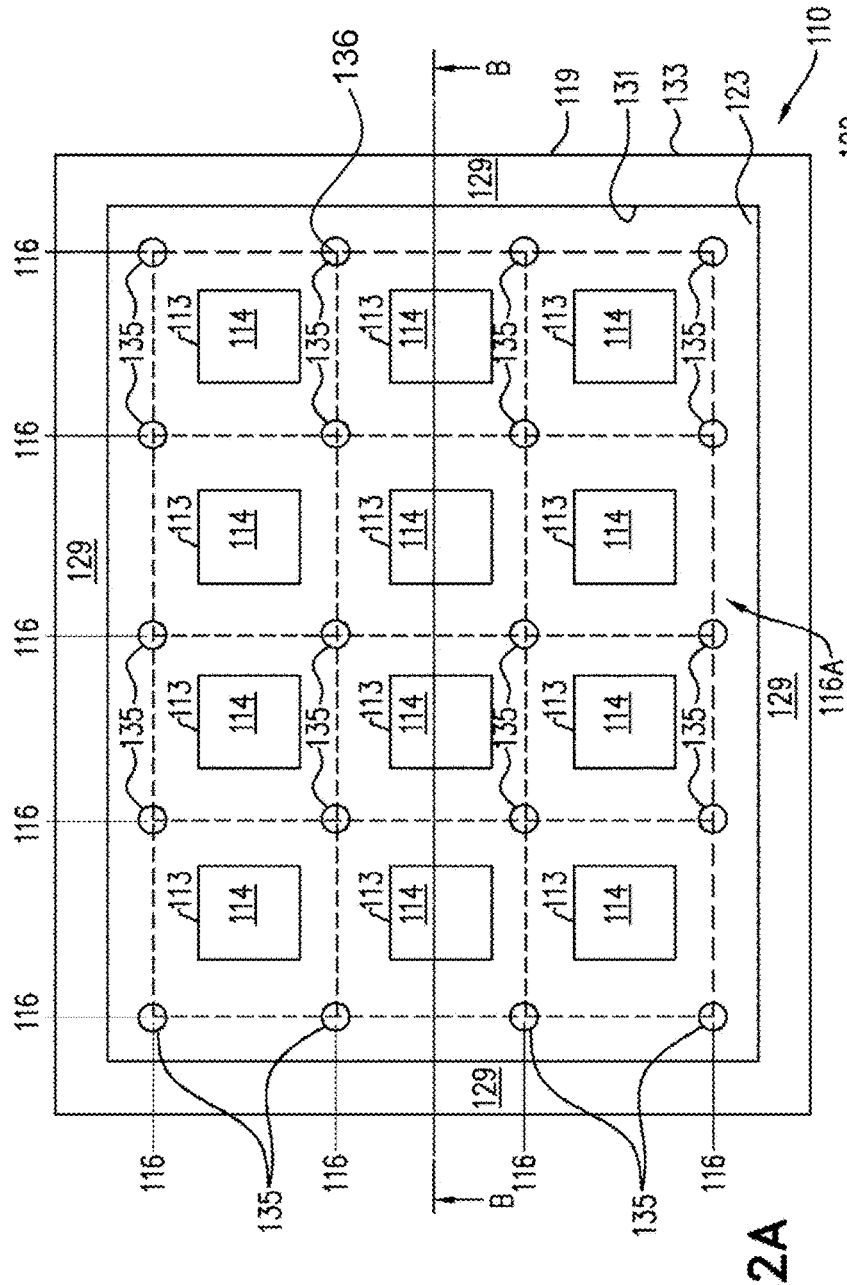
FIG. 2A is a top view of a patch in accordance with another example of the presently disclosed subject matter.
Figure 2B:
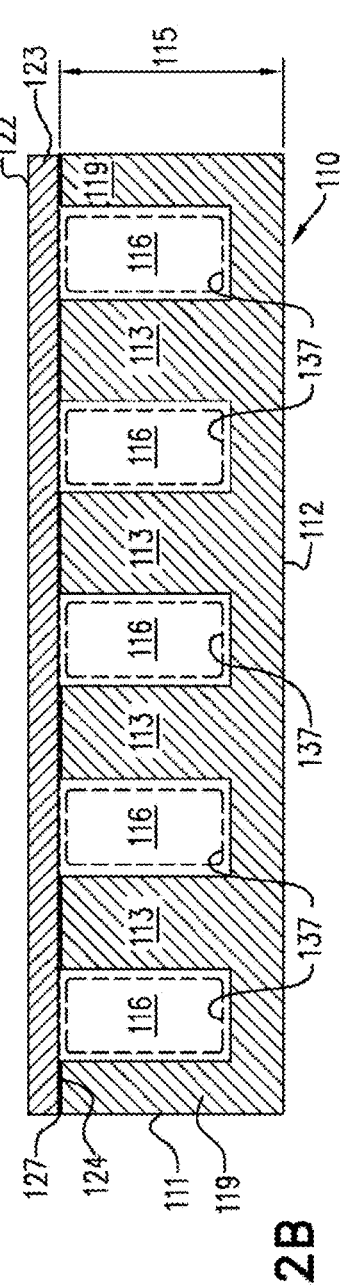
FIG. 2B is a cross-section of the patch of FIG. 2A, taken along line B-B in FIG. 2A.

Exemplary patch 110 shown in FIGS. 2A and 2B is an example of such a patch. It will be appreciated that the patch 110 is the same as the patch 10 shown in FIGS. 1A, 1B and 1C, with the addition of the sealing layer 123. FIG. 2A shows a top view of the exemplary patch 110, which corresponds to FIG. 1B, which shows a top view of the exemplary patch 10. It is noted that elements of the patch 110 which correspond to elements of the patch 10 have the same reference numbers as those in the patch 10, increased by 100.

FIG. 2B shows a cross-section of the patch 110 of FIG. 2A, taken where indicated by the letters B in FIG. 2A. The sealing layer 123 can be seen in FIG. 2B to be disposed along the projections plane 127 of the pressure-absorbing member 111 of the patch 110, and connected to the plurality of projections 113 of the pressure-absorbing member 111 so as to enclose the channels 116 and form enclosed channels 137 between the projections 113.

It will be appreciated further that in the exemplary patch 110 shown in FIGS. 2A and 2B, in addition to abutting the outermost surfaces 114 of each of the projections 113, the sealing layer 123 also abuts the outermost surfaces 129 of the outer bounding wall 119.

It will be appreciated that in the view of FIG. 2A, the sealing layer 123 lies across the entire area of the patch 110, and accordingly, the projections 113 and the line designating the inner surface 131 of the outer bounding wall 119 are indicated by dashed lines, as they are obscured in FIG. 2A by the sealing layer 123.

However, it will further be appreciated that in accordance with the presently disclosed subject matter, as will be explained in further detail below, the sealing layer 123 can be transparent or partially transparent, so that while the outermost surfaces 114 of the projections 113 and the outermost surfaces 129 of the outer bounding wall 119 are obscured as the sealing layer 123 is disposed on top of them, a degree of visibility of the plurality of the channels 116 of the array of channels 116A through the sealing layer 123 remains.

It will further be appreciated, as can be seen in FIG. 2B, that the sealing layer 123 serves to enclose the channels 116 of the array of channels 116A so as to form a closed channel 137 of each channel 116.

The exemplary patch 110 shown in FIGS. 2A and 2B is shown to further comprise fluid reservoirs 135 disposed along the plurality of channels 116 of the array of channels 116A. The fluid reservoirs 135 disposed in the plurality of channels 116 of the exemplary patch 110 can be seen to be disposed at the plurality of intersections 117 between the plurality of channels 116. It will be appreciated that the locations of the intersections 117 in FIG. 2A correspond to the locations of intersections 17 in FIG. 1B, although for the sake of clarity, the intersections 117 in FIG. 2A are not labeled due to overcrowding of the figure.

In accordance with the presently disclosed subject matter, the fluid reservoirs 135 contain a fluid, and the patch 110 is configured such that when the projections 113 are deformed under an external pressure applied upon at least a portion of a surface of the patch 110, the fluid is propelled from the fluid reservoir 135 so as to flow into at least one of the channels 116. It will be appreciated that a frictional force between the fluid and channel walls of the channel or channels 116 in which the fluid flows, absorbs at least a portion of the external pressure applied to the patch 110. Thus, at least a portion of the mechanical energy delivered to the patch via the external pressure applied to the patch, is absorbed by the patch, and not transmitted to the skin.

The fluid can be a colored fluid, and as mentioned previously, the sealing layer 123 can be transparent or partially transparent so that the flow of the fluid in the enclosed channels 137 can provide a visual indication of the pressure being exerted on the patch which can be monitored by a caregiver.

It will be appreciated that different examples of a patch in accordance with the presently disclosed subject matter, having the pressure indication feature described above, can be configured such that a measure of dispersion of the colored fluid in the channels can indicate a measure of the pressure applied to the patch.

Figure 12:
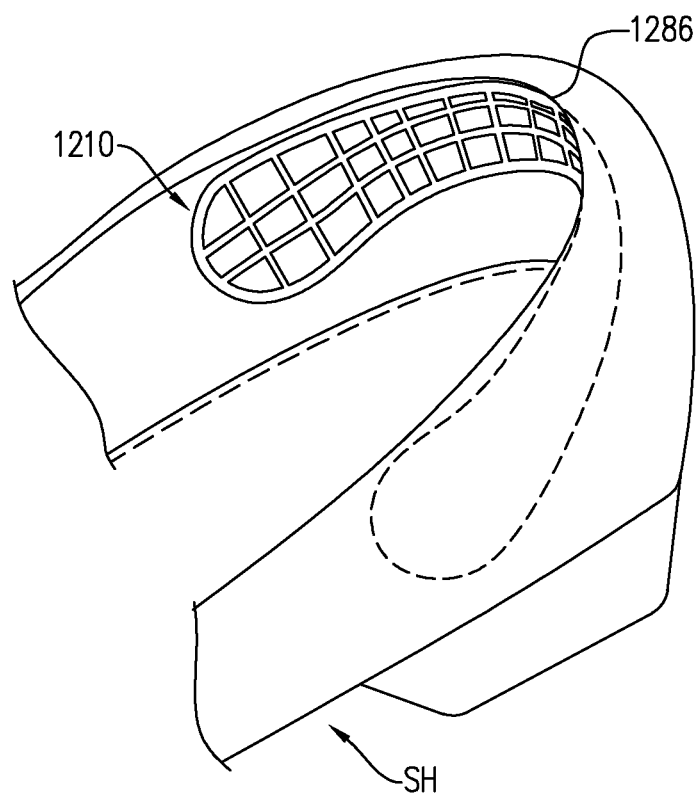
FIG. 12 is a top perspective view of an article of footwear fitted with a heel pad according to an example of the disclosure.

FIG. 12 shows one example of a patch such as patch 110 shown in FIGS. 2A and 2B, serving as a heel pad, configured to be attached to the back of a shoe, so as to absorb pressure applied by the back of the shoe to the area of the Achilles tendon at the back of the foot.

As shown in FIG. 12, the exemplary pad 1210 is attached by an adhesive to the inside back area 1286 of the shoe SH, so as to provide protection to the heel (and optionally to the Achilles tendon area at the back of a foot; not shown) which would be inserted into the shoe SH. The pad 1210 could thus absorb pressure applied by the back area 1286 of the shoe SH to the Achilles tendon area at the back of the foot inserted into the shoe SH.

In additional embodiments of a patch according to the presently disclosed subject matter, the sealing layer, such as the sealing layer 123 of the exemplary patch 110 shown in FIG. 2B, can be an additional pressure-absorbing member, such as the pressure-absorbing member 11 of the exemplary patch 10 shown in FIGS. 1A, 1B, and 1C, the pressure-absorbing member 111 of the exemplary patch 110 shown in FIGS. 2A and 2B, the pressure-absorbing member 411 of the exemplary patch 410 shown in FIG. 14A, the pressure-absorbing member 1411 of the exemplary patch 1410 shown in FIG. 14B, or any other pressure absorbing member.

Figure 3:
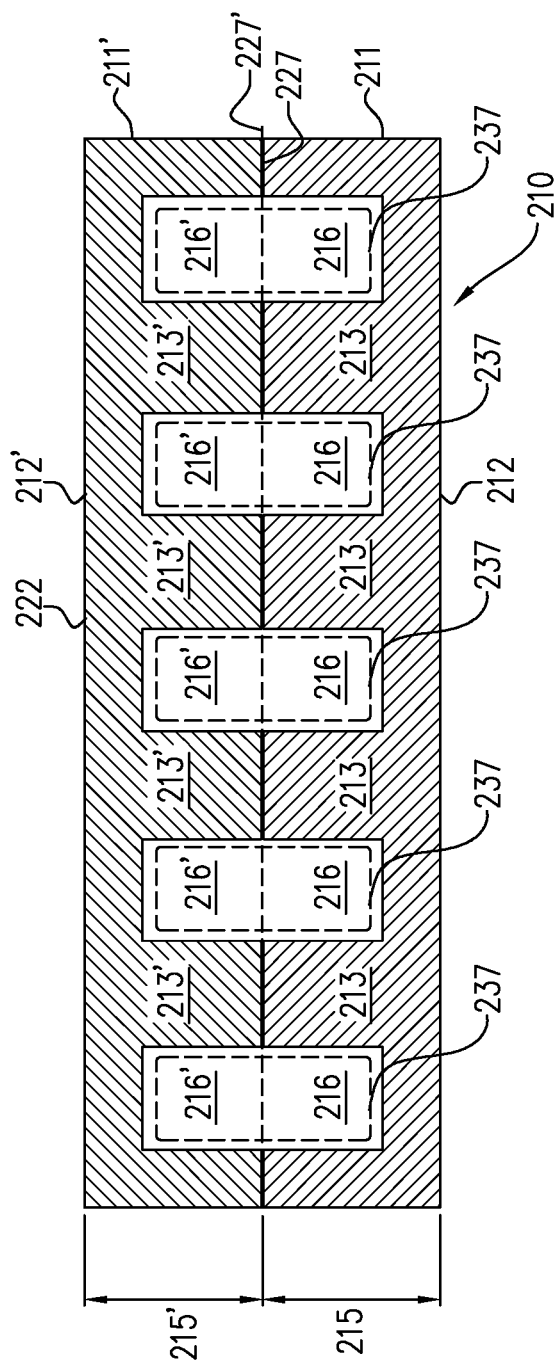
FIG. 3 is a cross-section of a patch in accordance with another example of the presently disclosed subject matter.
Figure 15:
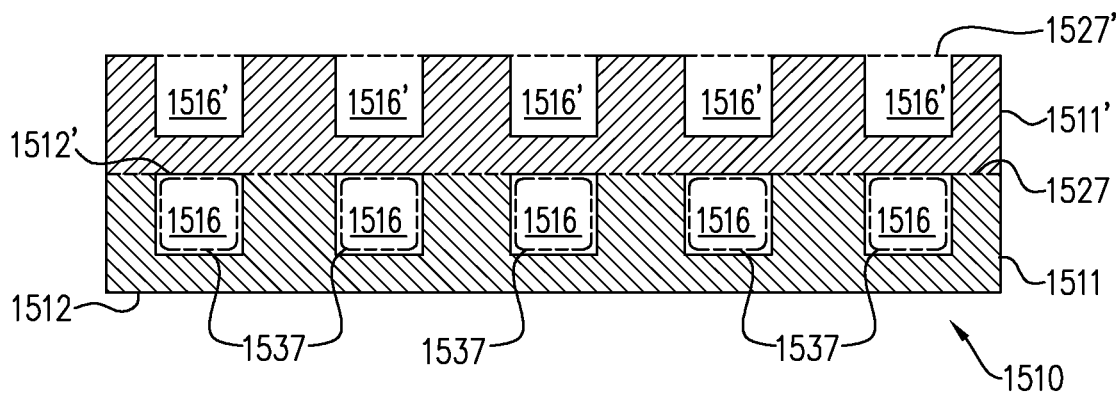
FIG. 15 is a cross-section of a patch in accordance with even another example of the presently disclosed subject matter.

Examples of such a patch are shown in FIG. 3 and FIG. 15. FIG. 3 shows a cross-section of an exemplary patch 210, which is similar to the cross-section of the patch 110 shown in FIG. 2B. It will be appreciated that elements of the patch 210 which correspond to elements of the patch 110 have the same reference numbers as the corresponding elements of the patch 110 in FIG. 2B, increased by 100.

As shown in FIG. 3, the patch 210 comprises a first pressure-absorbing member 211, and it differs from the patch 110 in that the sealing layer of the patch 210 is an additional pressure-absorbing member 211' which is identical to the first pressure-absorbing member 211. The first pressure-absorbing member 211 and the additional pressure-absorbing member 211' are oriented with respect to one another in a face-to-face manner, such that the projections plane 227 of the first pressure absorbing member 211 faces the projections plane 227' of the additional pressure-absorbing member 211'. Like the sealing layer 123 of the patch 110, the additional pressure-absorbing member 211' serves to enclose the channels 216 so as to form an enclosed channel 237 of each channel 216.

More specifically, in the case of a face-to-face orientation of identical pressure-absorbing members, as shown in FIG. 3, the enclosed channels 237 are formed by the channels 216 of the first pressure-absorbing member 211, which form the bottom half of the enclosed channels 237, while the channels 216' of the second pressure-absorbing member 211' form the upper half of the enclosed channels 237. It will be appreciated that the outermost surfaces 214 and 214' of the projections 213, cannot be seen in FIG. 3, as they abut each other and are therefore not visible.

It will be appreciated that one or both of the pressure-absorbing members 211 and 211' of the patch 210 can be transparent or semi-transparent like the sealing layer 123 of the patch 110 described above with respect to FIGS. 2A and 2B, and that the patch 210 can have one or more fluid reservoirs 235 and one or more intersections 217 like the fluid reservoirs 135 and the intersections 117 of the patch 110 described above with respect to FIGS. 2A and 2B, so that the patch 210 can be endowed with the visual pressure indicating capabilities described above with respect to the patch 110 of FIGS. 2A and 2B.

An additional embodiment of a patch in which the sealing layer is an additional pressure-absorbing member can be similar to the exemplary patch 210 shown in FIG. 3, except that its first pressure-absorbing member and its additional pressure-absorbing member can be oriented with respect to one another in a face-to-back manner, as shown in FIG. 15.

Such a patch, exemplary patch 1510, is shown in FIG. 15. It will be appreciated that elements of the patch 1510 which correspond to elements of the patch 210 have the same reference numbers as the corresponding elements of the patch 210 shown in FIG. 3, increased by 1300.

As shown in FIG. 15, the patch 1510 comprises a first pressure-absorbing member 1511, and an additional pressure-absorbing member 1511' similar to the first pressure-absorbing member 211 and the additional pressure-absorbing member 211' comprising the patch 210 shown in FIG. 3. However, rather than being oriented with respect to one another in a face-to-face manner along their respective projections planes 1527 and 1527', like the pressure-absorbing members 211 and 211' of FIG. 3, the pressure-absorbing members 1511 and 1511' of the patch 1510 are oriented with respect to one another in a face-to-back manner, such that the projections plane 1527 of the pressure absorbing member 1511 faces in the same direction as the projections plane 1527' of the additional pressure-absorbing member 1511'.

Accordingly, the enclosed channels 1537 formed by the enclosure of the channels 1516 by the first surface 1512' of the additional pressure-absorbing member 1511', are more similar to the enclosed channels 137 of the patch 110 of FIG. 2B than to the enclosed channels 237 of the patch 210 of FIG. 3, as only the channels 1516 of the first pressure-absorbing member 1511 are enclosed so as to form the enclosed channels 1537, rather than a combination of the channels of both of the pressure-absorbing members, as in the patch 210 of FIG. 3. As shown in FIG. 15, the channels 1516' of the additional pressure-absorbing member 1511' remain unsealed by any sealing layer or additional pressure-absorbing member, and therefore remain open channels.

It will be appreciated that in yet an additional embodiment of the patch according to the presently disclosed subject matter, yet an additional sealing layer or additional pressure-absorbing member of any suitable configuration could by attached to the projections plane 1527' of the patch 1510 in FIG. 15, or to any of the projections planes or patch surfaces in the examples of patches which are shown in this specification to be an engaging surface of a patch, i.e., to be an outermost surface of a patch not having an additional patch layer attached to it.

Figure 16:
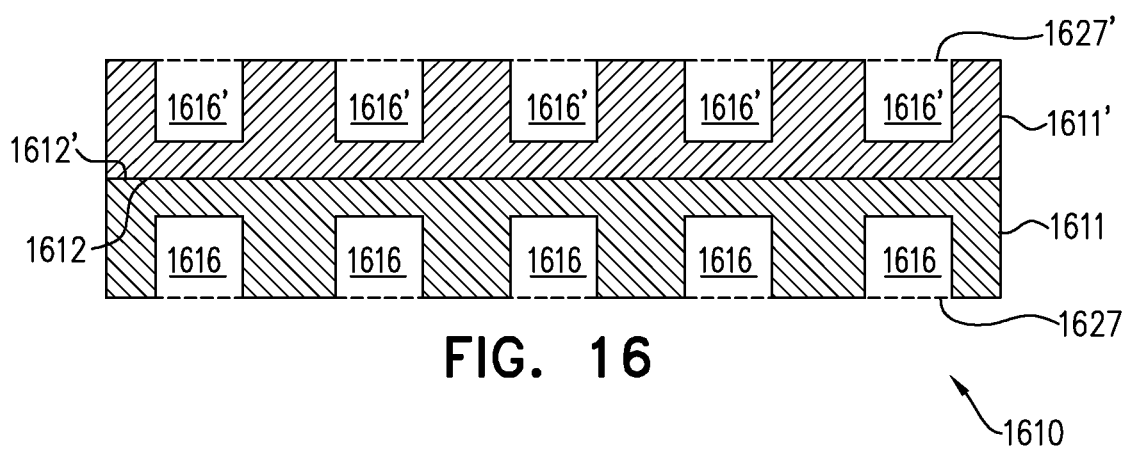
FIG. 16 is a cross-section of a patch in accordance with yet another example of the presently disclosed subject matter.

Yet an additional embodiment of a patch comprising a first pressure-absorbing member and an additional pressure-absorbing member is exemplary patch 1610 shown in FIG. 16. It will be appreciated that the patch 1610 shown in FIG. 16 is similar to the patches 210 and 1510 shown in FIGS. 3 and 15 respectively, as it also comprises an additional pressure-absorbing member attached to a first pressure-absorbing member. It will appreciated that elements of the patch 1610 which correspond to elements of the patch 1510 have the same reference numbers as the corresponding elements of the patch 1510 shown in FIG. 15, increased by 100.

However, the patch 1610 differs from the patches 210 and 1510 shown in FIGS. 3 and 15 respectively, in that its first pressure-absorbing member 1611 and its additional pressure-absorbing member 1611' are oriented with respect to one another in a back-to-back manner, such that the projections plane 1627 of the first pressure absorbing member 1611 faces in an opposite direction and away from the projections plane 1627' of the additional pressure-absorbing member 1611', as shown in FIG. 16.

It will be appreciated that the while the additional pressure-absorbing member 1611' is an additional pressure-absorbing member attached to a first pressure absorbing member, similar to the additional pressure-absorbing members 211' as 1511' of patches 210 and 1510 shown in FIGS. 3 and 15 respectively, however, the additional pressure-absorbing member 1611' cannot technically be considered to be a sealing layer, like the additional pressure-absorbing members 211' and 1511' of patches 210 and 1510 shown in FIGS. 3 and 15 respectively, since the additional pressure-absorbing member 1611' does not serve to enclose the channels 1616 so as to form enclosed channels in the patch 1610, as the additional pressure-absorbing members 211' as 1511' do in their respective patches 210 and 1510.

Rather, like the channels 1516' of the patch 1510, both the channels 1616 of the first pressure absorbing member 1611, as well as the channels 1616' of the additional pressure-absorbing member 1611', remain unsealed by any sealing layer or additional pressure-absorbing member, and therefore remain open channels, as shown in FIG. 16.

In yet even another embodiment of a patch according to the presently disclosed subject matter, at least one pressure-absorbing member of the patch can further comprise at least one medicament receptacle containing a medicament, and at least one medicament conduit extending from the medicament receptacle towards a surface of the patch, and wherein deformation of the projections of the pressure-absorbing member propels the medicament towards the surface of the patch via the medicament conduit or conduits.

Figure 4A:
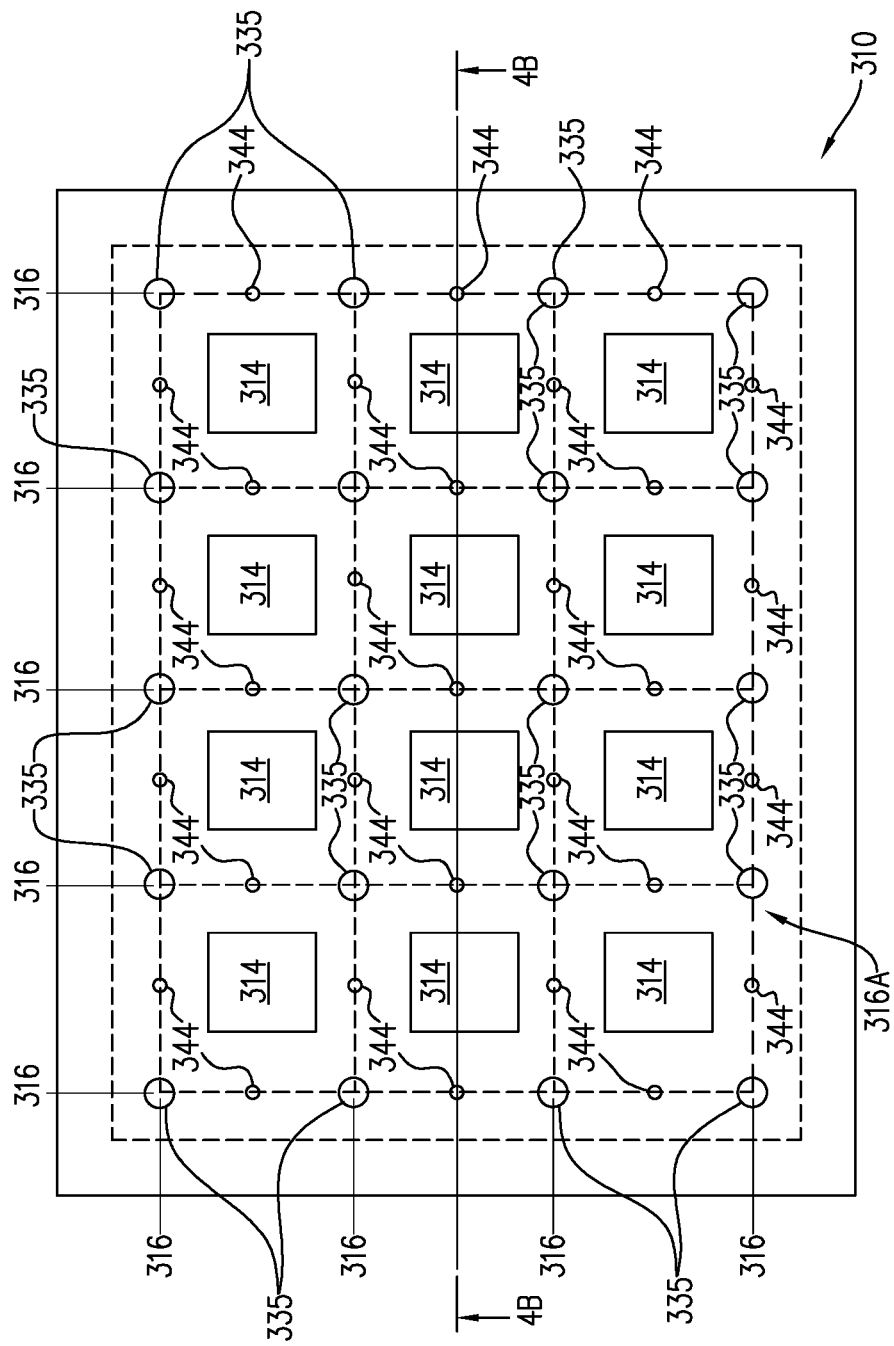
FIG. 4A is a top view of a patch in accordance with another example of the presently disclosed subject matter.
Figure 4B:
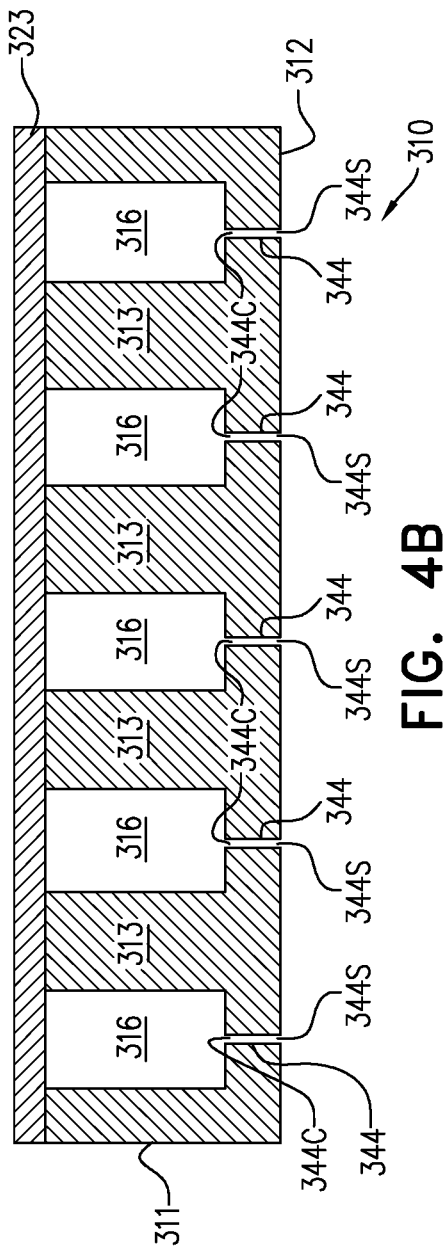
FIG. 4B is a cross-section of the patch of FIG. 4A, taken along line 4A-4A in FIG. 4A.

One example of such a patch, exemplary patch 310, is shown in FIGS. 4A and 4B.

FIG. 4A shows a top view of the exemplary patch 310, which corresponds to FIG. 2A, which shows a top view of the exemplary patch 110. FIG. 4B shows a cross-section of the exemplary patch 310, which corresponds to FIG. 2B, which shows a cross-section of the exemplary patch 110. It is noted that elements of the patch 310 which correspond to elements of the patch 110 have the same reference numbers as those in the patch 110, increased by 200.

The patch 310 is further configured in accordance with the presently disclosed subject matter to comprise at least one medicament conduit disposed in at least one channel of the plurality of channels of the patch. It can be seen in FIG. 4A that the exemplary patch 310 comprises a medicament conduit 344 along every segment of a channel 316 disposed between two reservoirs 335.

In accordance with the presently disclosed subject matter, each medicament conduit can have an opening at each one of its two opposite ends, wherein a first opening at a first end of each medicament conduit is disposed in a channel of the plurality of channels and wherein a second opening at a second end of the medicament conduit is disposed at a surface of the patch.

Accordingly, it can be seen in FIG. 4B that each medicament conduit 344 has a first opening 344C at its end which is disposed in a channel 316, and a second opening 344S at its opposite end which is disposed at the first surface 312 of the pressure-absorbing member 311.

It will be appreciated that the surface of a patch in accordance to the presently disclosed subject matter, at which the second openings of the medicament conduits can be disposed, such as the second openings 344S of the medicament conduits 344 of the exemplary patch 310, can be a skin-engaging surface of the patch, such that the medicament disposed in the patch can come into contact with the skin of the patient.

Figure 4C:
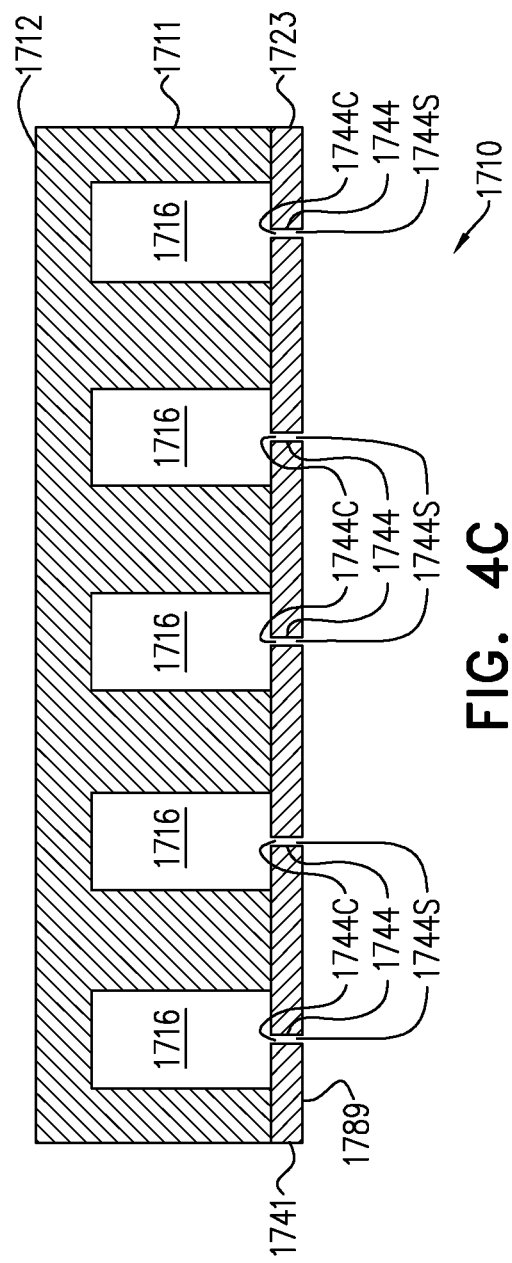
FIG. 4C is a cross-section of a patch in accordance with another example of the presently disclosed subject matter.

FIG. 4C shows a cross-section of an alternate embodiment of a patch having medicament conduits. It will be appreciated that the exemplary patch 1710 is similar to the exemplary patch 310 shown in FIGS. 4A and 4B, in that it comprises medicament conduits 1744, which correspond to the medicament conduits 344 of the patch 310. Each of the medicament conduits 1744 of the patch 1710 also has a first opening 1744C at its end which is disposed in a channel 1716, and a second opening 1744S at its opposite end which is disposed at a skin-engaging surface 1789 of the patch 1710.

However, the second openings 1744S of the medicament conduits 1744 are not disposed at the first surface 1712 of the pressure-absorbing member 1711. Rather, as can be seen in FIG. 4C, the pressure-absorbing member 1711 along with the sealing layer 1723 are in an inverted position in the patch 1710 with respect to the position of the pressure-absorbing member 311 along with the sealing layer 323 in the patch 310. Consequently, rather than being located in the pressure-absorbing member 1711, the medicament conduits 1744 are disposed in the sealing layer 1723, which, in the patch 1710 comprises the skin-engaging surface 1789 of the patch 1710, since, as mentioned above, the skin-engaging surface of a patch in accordance to the presently disclosed subject matter, is the surface of the patch at which the second openings of the medicament conduits are disposed, such that the medicament disposed in the patch can come into contact with the skin of the patient. Thus, the skin-engaging surface 1789 of the patch 1710 is the surface of the sealing layer 1723 at which the second openings 1744S of the medicament conduits 1744 are disposed.

It will be appreciated that a sealing layer comprising medicament conduits can be considered to be a medicament-delivery layer of a patch in accordance with the presently disclosed subject matter. Thus, the sealing layer 1723 of the exemplary patch 1710 shown in FIG. 4C can be considered to be a medicament delivery layer 1741.

It will be appreciated that a patch according to an embodiment of the presently disclosed subject matter can have features described above in any combination thereof.

Figure 4D:
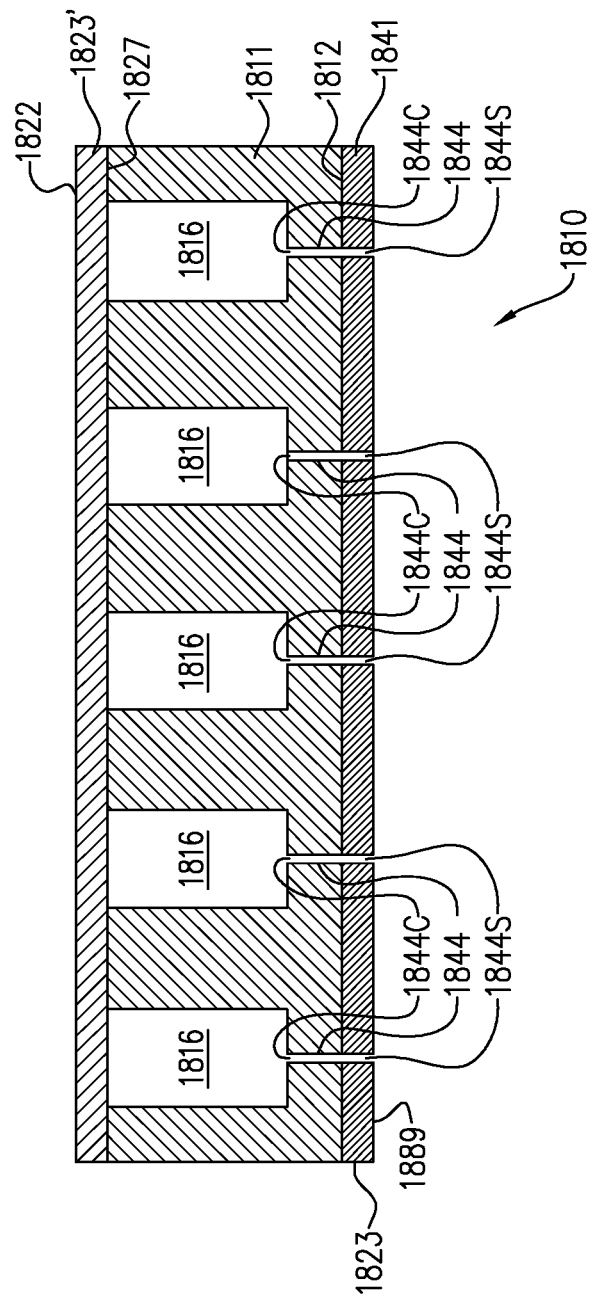
FIG. 4D is a cross-section of a patch in accordance with yet another example of the presently disclosed subject matter.

For example, as shown in FIG. 4D, which shows a cross-section of yet another alternate embodiment of a patch having medicament conduits, the exemplary patch 1810 can be seen to comprise a pressure-absorbing member 1811 similar to the pressure-absorbing member 311 of the patch 310 shown in FIG. 4B which has medicament conduits 344. The exemplary patch 1810 can further be seen to comprise a sealing layer 1823 comprising medicament conduits 1844, i.e., a medicament delivery layer 1841, similar to the sealing layer 1723 comprising medicament conduits 1744, i.e., the medicament delivery layer 1741, of the patch 1710 shown in FIG. 4C. The exemplary patch 1810 can yet further be seen to comprise an additional sealing layer 1823' disposed along the projections plane 1827 of the pressure-absorbing member 1811, so as to enclose the channels 1816.

Figure 5:
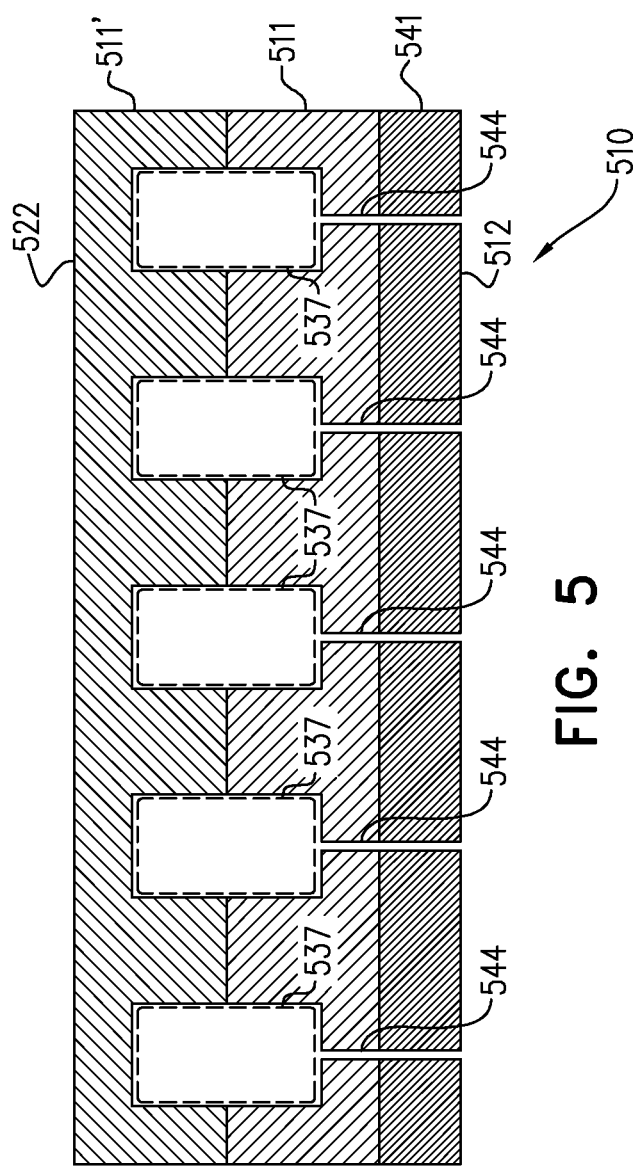
FIG. 5 is a cross-section of a patch in accordance with another example of the presently disclosed subject matter.

Another example of a patch according to an embodiment of the presently disclosed subject matter which combines features described above is the exemplary three-layer patch 510 shown in FIG. 5. The exemplary patch 510 comprises two identical pressure-absorbing members 511 and 511' similar to the identical pressure-absorbing members 211 and 211' of the patch 210 shown in FIG. 3. The exemplary patch 510 can further be seen to comprise a medicament delivery-layer 541, similar to the medicament delivery-layers 1741 and 1841 of the respective patches 1710 and 1810 shown in FIGS. 4C and 4D respectively.

Figure 9:
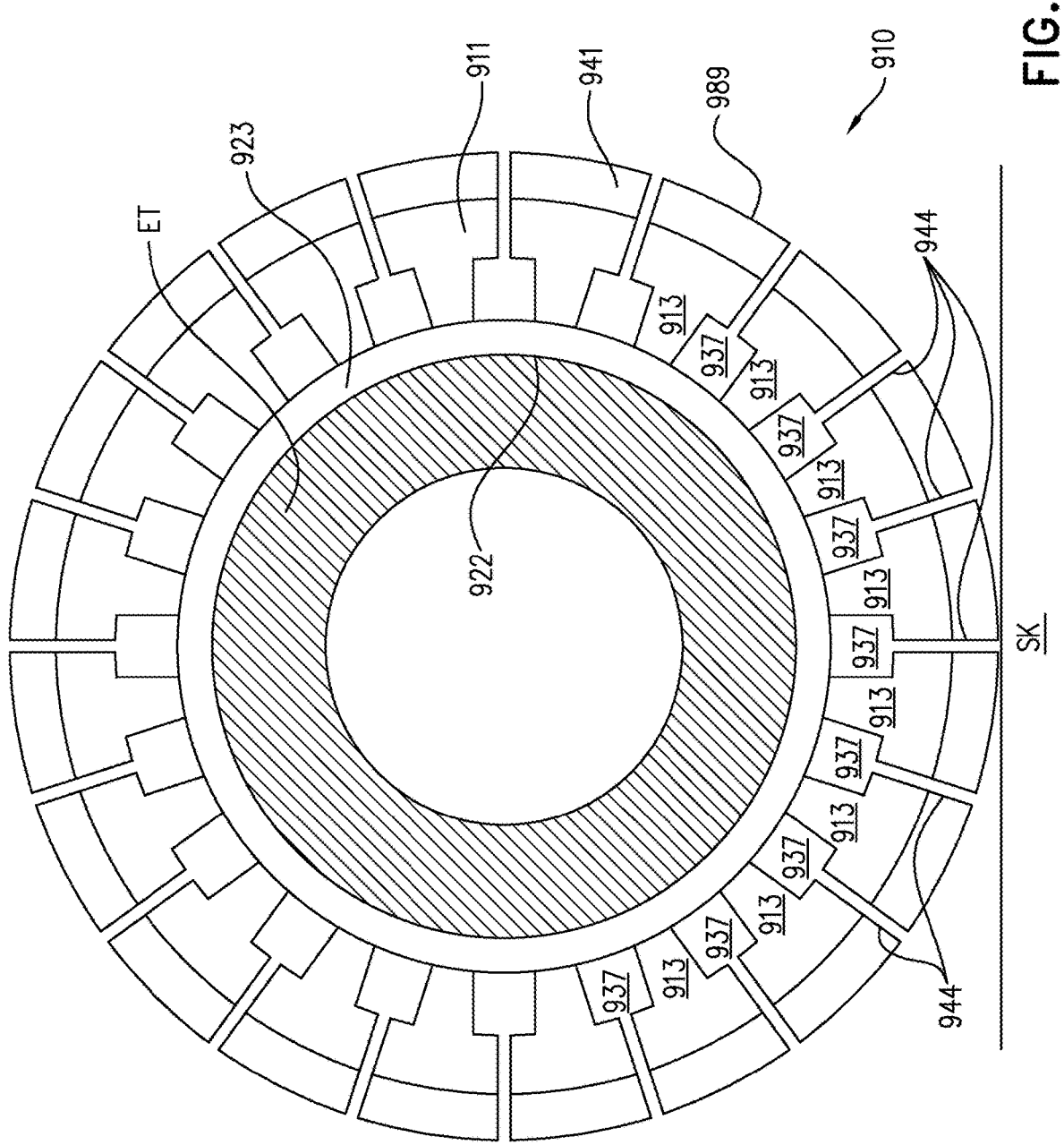
FIG. 9 is a cross-section of a patch in accordance with another example of the presently disclosed subject matter, shown in use with an endotracheal tube.

FIG. 9 shows yet another embodiment of a patch according to the presently disclosed subject matter, in which a patch such as the patch 1810 of FIG. 4D is wrapped around an endotracheal tube to form a patch 910 in the shape of a tube. It will be appreciated that the patch 910 is the same as the patch 1810 shown in FIG. 4D, with elements corresponding to the elements of the patch 1810 having the same reference numerals as the elements of the patch 1810, decreased by 900.

Thus, the endotracheal tube ET can be seen in FIG. 9 to be disposed at the center of the tube-shaped patch 910, which can be seen to comprise three layers, and which protects the skin SK from pressure exerted upon it by the endotracheal tube ET by being interposed between the endotracheal tube ET and the skin SK.

Like the patch 1810, the tube-shaped patch 910 comprises a medicament delivery-layer 941 which comprises the skin-engaging surface 989 of the patch 910. Disposed adjacent to the skin SK so as to be in a position to deliver a medicament to the skin SK, the medicament delivery-layer 941 is the outermost layer of the tube-shaped patch 910.

As can be seen in FIG. 9, the medicament delivery-layer 941 of the patch 910 comprises medicament conduits 944 for delivery of a medicament or medicaments from the enclosed channels 937 to the skin SK. It will be appreciated that the medicament conduits 944 are disposed all along the skin-engaging surface 989 of the tube-shaped patch 910, even though only a portion of the tube-shaped patch 910 can be seen to be in close proximity to the skin SK. It will be appreciated that this is the case so that contact between medicament conduits 944 and the skin SK can be assured regardless of how the endotracheal tube ET along with the tube-shaped patch 910 is positioned along the skin SK by a care provider, and regardless of movements of the patient, the tubing or other equipment, which can change the position of the endotracheal tube ET along with the tube-shaped patch 910, with respect to the skin SK.

Thus, the care provider (e.g. nurse, physician, anesthesiologist etc.) need not position the patch in a specific orientation in order to achieve the full protective effect of the patch during use, i.e. maximal access of medicament conduits in the patch to the skin. Likewise, medicament conduits can remain in contact with the skin regardless of a change of position or orientation of the patch associated with the application technique of the patch, or movements of the patient or any equipment.

It will be appreciated that the medicament delivery-layer 941 of the patch 910, as the outermost layer of the patch 910, can be configured to be transparent or partially transparent, in order to allow observation of the flow of the fluid in the enclosed channels 937 through the medicament delivery-layer 941.

Figure 10:
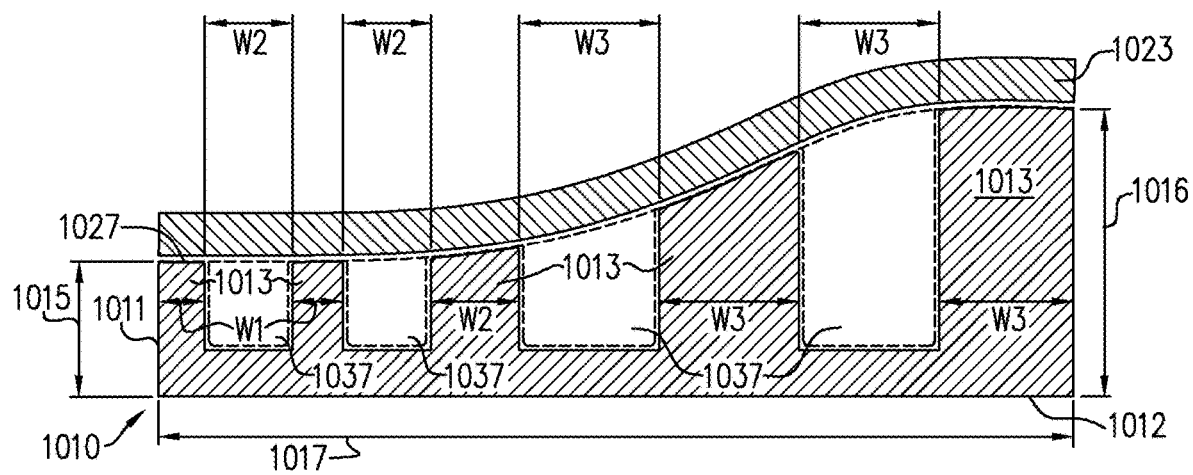
FIG. 10 is a cross-section of a patch in accordance with another example of the presently disclosed subject matter.

FIG. 10 shows yet another embodiment of a patch according to the presently disclosed subject matter. The patch 1010 shown in FIG. 10 is similar to the patch 110 shown in FIGS. 2A and 2B, but as shown in FIG. 10, the thickness of the pressure-absorbing member 1011 varies from a minimal thickness 1015 to a maximal thickness 1016, and the sealing layer 1023 curves along the projections plane 1027 along the length 1017 of the patch 1010 between the minimal thickness 1015 to the maximal thickness 1016 of the patch 1010. Furthermore, the projections 1013 of the patch 1010 have varying widths of W1, W2 and W3, and the enclosed channels 1037 also have varying widths of W2 and W3.

Figure 11:
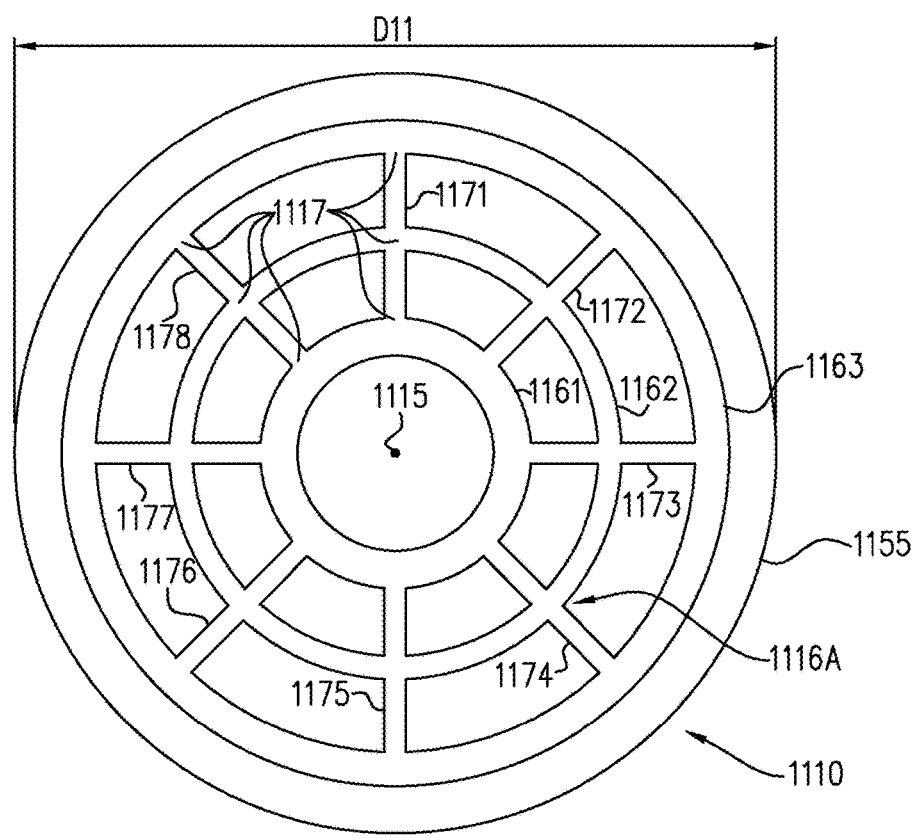
FIG. 11 is a top view of a patch in accordance with another example of the presently disclosed subject matter.

FIG. 11 shows yet another embodiment of a patch according to the presently disclosed subject matter. The patch 1110 shown in FIG. 11 has a circular shape rather than a rectangular shape, and it can be described by a single dimension, i.e., a diameter, rather than two dimensions, i.e., a length and a width. The patch 1110 in FIG. 11 can be seen to have a central point 1115, a diameter DK and an outermost extent 1155 defined by the diameter D11.

As shown in FIG. 11, the array of channels 1116A of the patch 1110 comprises three concentric annular channels 1161, 1162 and 1163 disposed at a distance from one another between the innermost annular channel 1161 disposed at a minimal distance from the central point 1115 of the patch, and the outermost annular channel 1163 disposed at a minimal distance from the outermost extent 1155 of the patch. As shown in FIG. 11, the array of channels 1116A of the patch 1110 further comprises eight radiating channels 1171, 1172, 1173, 1174, 1175, 1176, 1177, and 1178 extending in a radiating manner from the innermost annular channel 1161 to the outermost annular channel 1163, and disposed at a distance from one another.

The patch 1110 can further have one or more reservoirs 1135 disposed at one or more intersections of the twenty-four intersections 1117 between the annular channels 1161, 1162 and 1163 and the radiating channels 1171, 1172, 1173, 1174, 1175, 1176, 1177, and 1178.

Figure 13:
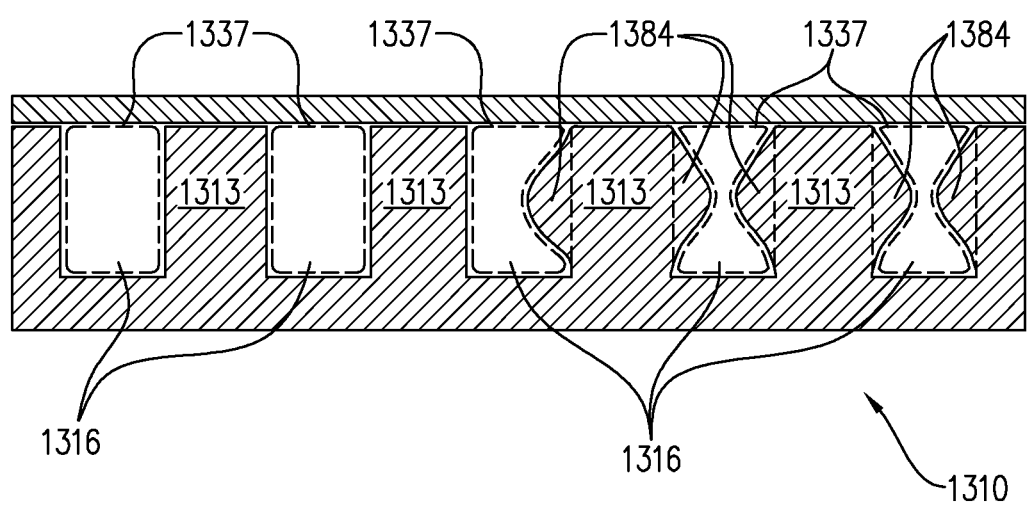
FIG. 13 is a cross-section of a patch in accordance with another example of the presently disclosed subject matter.

FIG. 13 shows yet another embodiment of a patch according to the presently disclosed subject matter, having obstructions in a portion of its channels, thereby increasing the resistance imposed on the fluid flow in those channels, and hence the resulting energy dissipation in the area of the patch in which the partially obstructed channels are located.

It will be appreciated that the patch 1310, a cross-section of which is shown in FIG. 13, is similar to the patch 110 shown in FIGS. 2A and 2B, with the addition of obstructions in the channels 1316. It will be appreciated that the cross-section of the patch 1310 shown in FIG. 13 corresponds to the cross-section of the patch 110 shown in FIG. 2B. It is noted that elements of the patch 1310 which correspond to elements of the patch 110 have the same reference numbers as those in the patch 110, increased by 1200.

It can be seen in FIG. 13 that the middle channel 1316 and the two channels 1316 on the right-hand side of the patch 1310 are obstructed with respect to the two channels 1316 on the left-hand side of the patch 1310. The obstructions in the obstructed channels 1316 can be seen to be formed by the protrusions 1384 protruding from the projections 1313 into the channels 1316. Each of the two right-hand channels 1316 can be seen to be obstructed by two protrusions 1384, a protrusion 1384 protruding from each wall of the two right-hand channels 1316. The middle channel 1316 can be seen to be obstructed by only one protrusion 1384, protruding from the right-hand wall of the middle channel 1316.

It can further be seen in FIG. 13 that an unobstructed cross-sectional area available for fluid to flow through, of the enclosed channels 1337 of the channels 1316 is reduced in the obstructed middle channel 1316 and the two right-hand channels 1316 with respect to the unobstructed two left-hand channels 1316. Specifically, it can be seen in the figure that the unobstructed cross-sectional areas available for fluid to flow through of the two right-hand enclosed channels 1337 has been reduced to the hourglass shape shown in the figure, which is constricted in the middle in comparison with the unobstructed rectangular cross-sectional area of the two left-hand enclosed channels 1337. It can further be seen in the figure that the unobstructed cross-sectional area available for fluid to flow through of the middle enclosed channel 1337 has only been reduced on its right side, where the protrusion 1384 protrudes into the channel.

The presently disclosed subject matter further includes a method of producing a patch comprising two layers, each of which is a pressure-absorbing member formed of a resilient material and having at least a first surface, wherein the at least first surface is configured with a plurality of projections extending therefrom and a plurality of channels crossing one another at a plurality of intersections, and wherein an outermost surface of the plurality of projections lies along a projections plane of each pressure-absorbing member, the projections being deformable when subjected to pressure applied to the patch, so as to absorb at least some of the applied pressure. The patch further comprises one or more reservoirs disposed along one or more channels of the plurality of channels, the plurality of channels and the one or more reservoirs constituting a network of channels and reservoirs of each of the two pressure-absorbing members.

Figure 6:
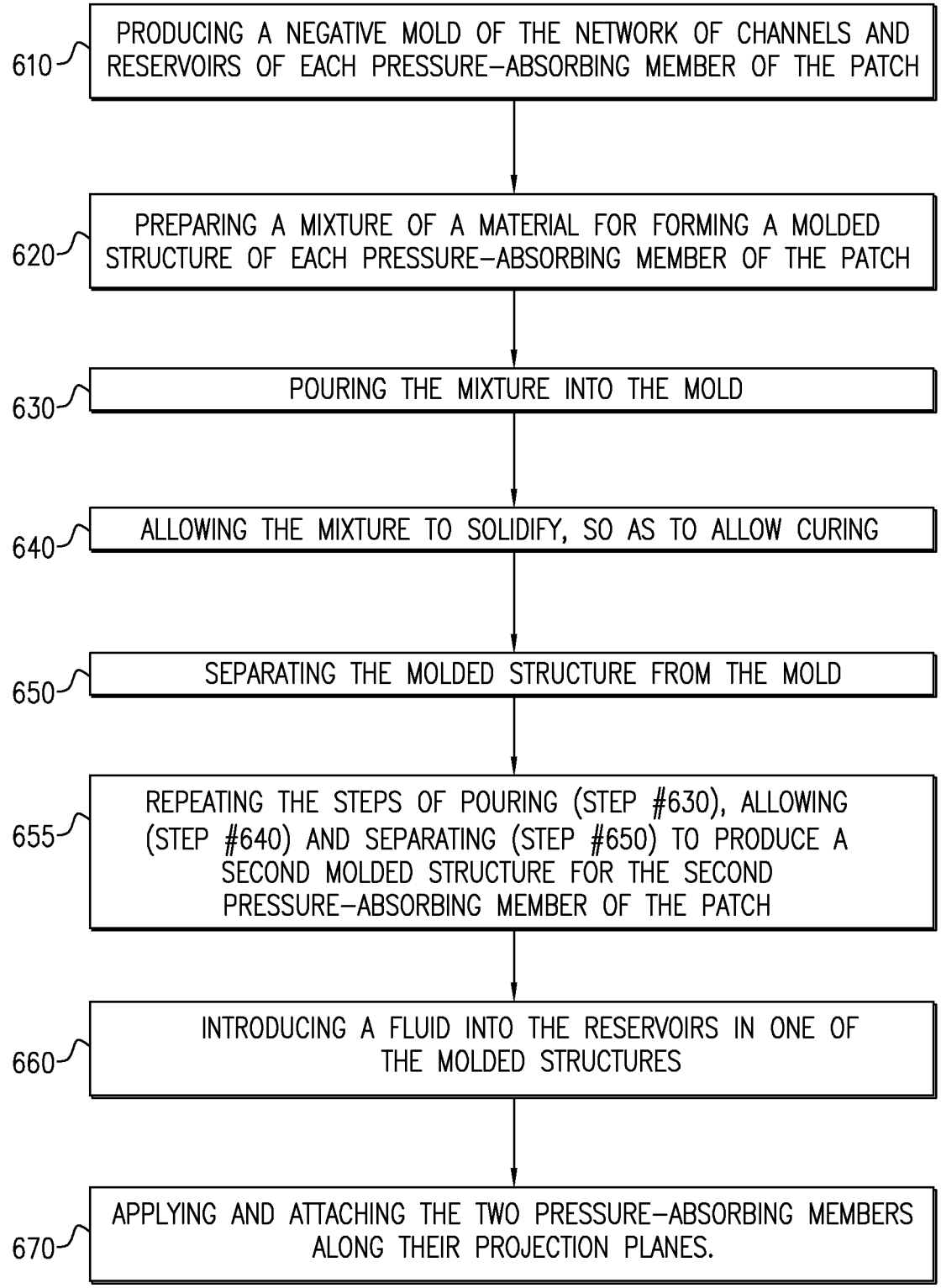
FIG. 6 is a flow diagram illustrating one example of a method, by which a two-layer patch according to the presently disclosed subject matter can be produced.

As illustrated in FIG. 6, the method comprises seven main steps 610, 620, 630, 640, 650, 660 and 670. An intermediate step, step 655 comprises the repetition of the main steps 630, 640, and 650 as will be explained below.

In the first main step of the method, step 610, a negative mold of the network of channels and reservoirs of each of the two pressure-absorbing members of the patch is produced, for example by three-dimensional (3D) printing. In the second main step, step 620, a mixture of a material for forming a molded structure of each of the two pressure-absorbing members is prepared. In the third main step, step 630, the mixture is poured into the mold. In the fourth main step, step 640, the mixture is allowed to solidify so as to cure, for example, at room temperature. In the fifth main step, step 650, the molded structure is separated from the mold. In the intermediate step, step 655, the main steps 630, 640, and 650 are repeated in order to produce a second molded structure for the second pressure-absorbing member of the patch. In the sixth main step, step 660, a fluid is introduced into the one or more reservoirs in one of the molded structures. In the seventh and final main step, step 670, the two molded structures are applied and attached to one another along their projections planes.

The presently disclosed subject matter further includes a method of producing a patch comprising three layers, each layer of the three layers being at least partially formed of a resilient material, the patch comprising a middle layer disposed between a top sealing layer and a bottom medicament-delivery layer, the middle layer being a pressure-absorbing member having at least a first surface, wherein the at least first surface is configured with a plurality of projections extending therefrom and a plurality of channels crossing one another at a plurality of intersections, and wherein an outermost surface of the plurality of projections lies along a projections plane of the pressure-absorbing member, the projections being deformable when subjected to pressure applied to the patch, so as to absorb at least some of the applied pressure. The pressure-absorbing member further comprises one or more reservoirs disposed along one or more channels of the plurality of channels, the plurality of channels and the one or more reservoirs constituting a network of channels and reservoirs of the pressure-absorbing member. The pressure-absorbing member further comprises at least one medicament receptacle containing a medicament, and at least one medicament conduit extending from the medicament receptacle towards a surface of the pressure-absorbing member.

Figure 7:
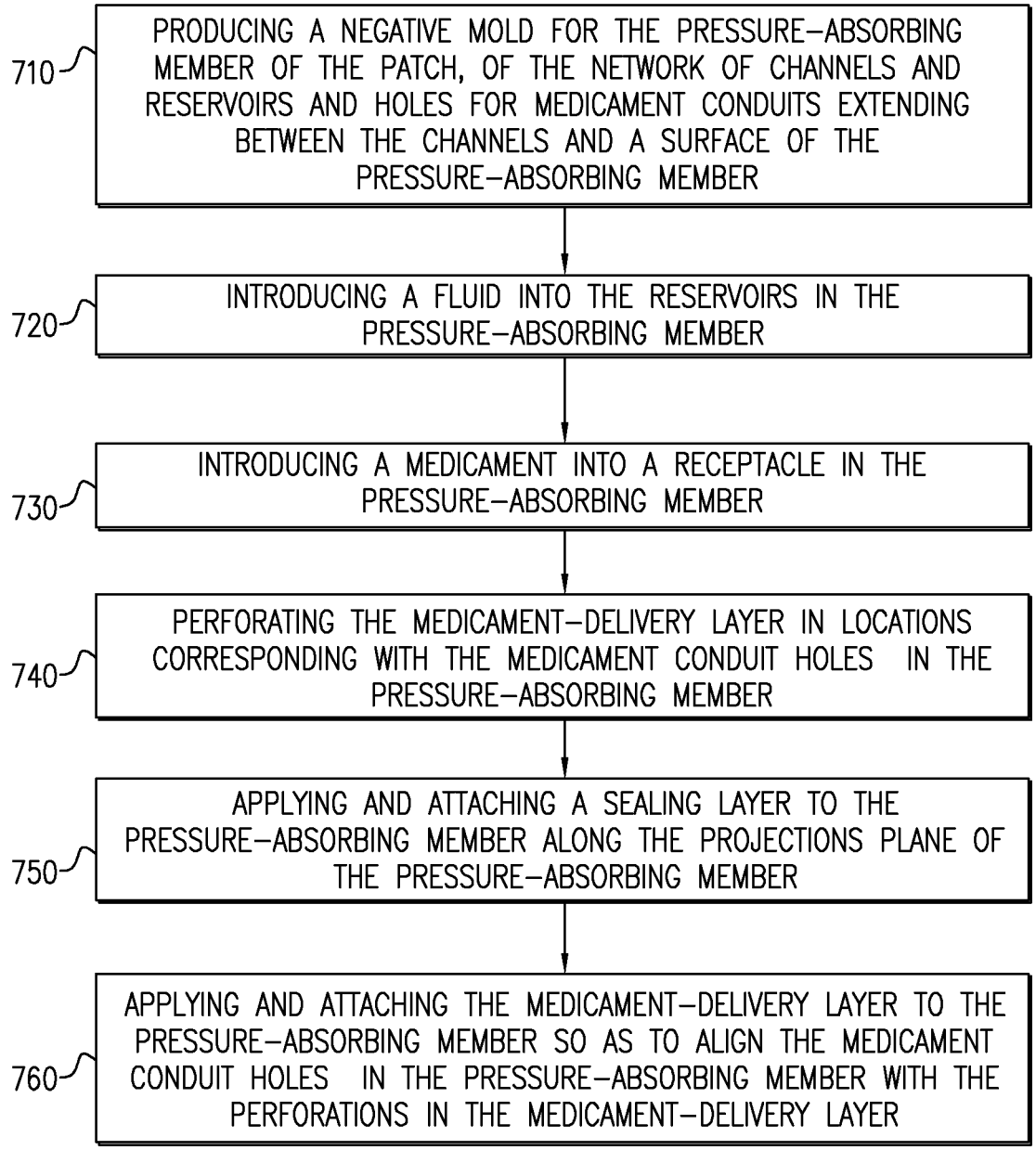
FIG. 7 is a flow diagram illustrating one example of a method, by which a three-layer patch according to the presently disclosed subject matter can be produced.

As illustrated in FIG. 7, the method comprises six main steps 710, 720, 730, 740, 750 and 760. In the first main step of the method, step 710, a negative mold of the network of channels and reservoirs of the pressure-absorbing member, as well as holes for medicament conduits extending between the channels and a surface of the pressure-absorbing member, is produced, for example by three-dimensional (3D) printing. In the second main step, step 720, a fluid is introduced into the one or more reservoirs in the pressure-absorbing member. In the third main step, step 730, a medicament is introduced into a receptacle in the network of channels and reservoirs in the pressure-absorbing member. In the fourth main step, step 740, the medicament delivery-layer is perforated so as to form perforations in locations of the medicament delivery-layer corresponding with the holes of the medicament conduits in the pressure-absorbing member. In the fifth main step, step 750, the sealing layer is applied and attached to the pressure-absorbing member along its projections plane. In the sixth and final main step, step 760, the medicament delivery-layer is applied and attached to the pressure-absorbing member so as to align the medicament conduit holes in the pressure-absorbing member with the perforations in the medicament delivery-layer.

The invention claimed is:

1. A patch comprising:
  at least one pressure-absorbing member, said pressure absorbing member formed of a continuous piece of resilient material and having:
    a first surface,
    a plurality of projections extending from said first surface,
    a plurality of channels crossing one another at a plurality of intersections,
    an outer bounding wall having an inner side surface facing the plurality of projections, said inner side surface and the plurality of projections define a plurality of outermost channels therebetween,
    wherein an outermost surface of said plurality of projections and of said outer bounding wall lies along a projections plane of said pressure-absorbing member, said plurality of projections being deformable when subjected to pressure applied to the patch, so as to absorb at least some of the applied pressure; and
    a resilient sealing material layer disposed along the projections plane and connected to the plurality of projections and/or the outer bounding wall so as to enclose the plurality of channels and form enclosed channels therebetween.

2. A patch according to claim 1, further comprising at least one fluid reservoir having one of the following configurations: the at least one fluid reservoir is disposed along at least one channel of the plurality of channels; the at least one fluid reservoir is disposed at least at one of the plurality of intersections; the at least one fluid reservoir contains a fluid and the patch is configured such that when the projections are deformed under an external pressure applied upon at least a portion of a surface of the patch, the fluid is propelled from the at least one fluid reservoir so as to flow into the at least one channel, wherein a frictional force between the fluid and channel walls of the at least one channel absorbs at least a portion of said external pressure.

3. A patch according to claim 2, wherein the fluid is either a viscous fluid, a colored fluid, a fluid configured to undergo a change in color as a consequence of contact with at least one of a second fluid and a coating on the channel walls, a fluid that has a specific heat capacity greater than that of skin of a patient, a fluid that has high thermal conductance rendering the fluid capable of functioning as a coolant after being refrigerated, a fluid that contains at least one freezing point depressant so as to improve efficacy of the fluid as a coolant after the fluid is refrigerated.

4. A patch according to claim 3, wherein a viscous flow of said viscous fluid absorbs at least an additional portion of said external pressure.

5. A patch according to claim 4, further comprising at least one resistance element disposed in at least one channel in the plurality of channels so as to increase at least one of said frictional force and an energy absorption of said viscous flow, and thereby at least of one of said portion of said external pressure and said additional portion of said external pressure.

6. A patch according to claim 5, wherein the at least one resistance element is one of a valve, an obstruction and a quantity of porous media.

7. A patch according to claim 2, wherein the fluid is contained in a capsule, wherein the capsule is configured to rupture when an external pressure exceeding a threshold capsule-rupturing pressure is applied upon a portion of a surface of the patch at least adjacent to the at least one reservoir.

8. A patch according to claim 1, wherein said patch is configured to have a patch stiffness matched to a skin stiffness of skin of a patient at a location of use of said patch.

9. A patch according to claim 8, wherein said patch stiffness is a weighted average of skin layer stiffness of multiple tissue layers at said location, wherein said weighted average is a sum of a product of said skin layer stiffness and a thickness of each of said multiple tissue layers divided by a total thickness of said multiple tissue layers.

10. A patch according to claim 1, wherein the continuous piece of resilient material and/or the resilient sealing material layer has at least one of the following properties: it is at least one of elastomer, soft polymer, polymer composite, polymer gel, silicone, silicone rubber, silicone gel, silicone foam, silicone sponge, rubber, gel, hydrogel, gel foam, gel sponge, foam, open-cell foam, closed-cell foam, and fabric; it has a specific heat capacity greater than that of skin of a patient; it has thermal conductivity greater than that of skin of a patient; and/or it has high thermal conductance for functioning as a coolant after being refrigerated.

11. A patch according to claim 1, configured to be secured by an adhesive material to at least a portion of a medical device which comes into contact with skin of a patient.

12. A patch according to claim 1, comprising articulation arrangements for articulation of the patch to a medical device.

13. A patch according to claim 1, configured to be disposed, at least indirectly, intermediate a patient and an external pressure applying member.

14. A patch according to claim 1, wherein one of said first surface and said projections plane of the pressure absorbing member is one of a pressure-engaging surface and a skin-engaging surface of the patch; and the other one of the first surface and the projections plane of the pressure absorbing member, is an other one of the pressure-engaging surface and a skin-engaging surface of the patch.

15. A patch according to claim 1, wherein the patch has a length and a width, and the plurality of channels comprises a first quantity of channels and a second quantity of channels, wherein the first quantity of channels is oriented in parallel with the length, wherein each channel of the first quantity is disposed at a distance from one another along the width of the patch, and wherein the second quantity of channels is oriented in parallel with the width of the patch, wherein each channel of the second quantity is disposed at a distance from one another along the length of the patch.

16. A patch according to claim 1, wherein at least one of the pressure-absorbing member and the sealing layer is at least semitransparent.

17. A method of manufacturing the patch of claim 1, the method comprising:
   obtaining a negative mold of the pressure-absorbing member;
   preparing a mixture of a material for forming the pressure-absorbing member;
   pouring said mixture into said mold;
   allowing the mixture to solidify;
   applying the resilient sealing material layer along said projections plane of the pressure-absorbing member and connecting said resilient sealing material layer to the plurality of projections, so as to enclose and seal the plurality of channels.

18. A method of absorbing, via the patch of claim 1, an external pressure exerted on a body by a pressure producing source, the method comprising:
   introducing the patch in-between said body and said pressure producing source, directly or indirectly, so as to allow said projections to deform when subjected to said external pressure, said projections thereby absorbing at least some of said external pressure.

* * * * *